United States Patent
Johnson et al.

(10) Patent No.: US 10,371,499 B2
(45) Date of Patent: Aug. 6, 2019

(54) LASER SWEPT SOURCE WITH CONTROLLED MODE LOCKING FOR OCT MEDICAL IMAGING

(75) Inventors: Bartley C. Johnson, North Andover, MA (US); Dale C. Flanders, Lexington, MA (US)

(73) Assignee: AXSUN TECHNOLOGIES, INC., Billerica, MA (US)

( * ) Notice: Subject to any disclaimer, the term of this patent is extended or adjusted under 35 U.S.C. 154(b) by 0 days.

(21) Appl. No.: 13/976,229

(22) PCT Filed: Dec. 27, 2011

(86) PCT No.: PCT/US2011/067413
§ 371 (c)(1),
(2), (4) Date: Sep. 11, 2013

(87) PCT Pub. No.: WO2012/092290
PCT Pub. Date: Jul. 5, 2012

(65) Prior Publication Data
US 2014/0085639 A1    Mar. 27, 2014

Related U.S. Application Data

(63) Continuation-in-part of application No. 12/979,225, filed on Dec. 27, 2010.

(51) Int. Cl.
*A61B 5/00* (2006.01)
*G01B 9/02* (2006.01)
(Continued)

(52) U.S. Cl.
CPC ........ *G01B 9/02091* (2013.01); *A61B 5/0066* (2013.01); *A61B 5/6852* (2013.01);
(Continued)

(58) Field of Classification Search
CPC .. A61B 5/0066; A61B 3/102; G01B 9/02091; G01N 21/4795
See application file for complete search history.

(56) References Cited

U.S. PATENT DOCUMENTS

| 3,339,073 A | 8/1967 | Hunter |
| 3,586,997 A | 6/1971 | Kinsel |

(Continued)

FOREIGN PATENT DOCUMENTS

| JP | 2002-511199 A | 4/2002 |
| JP | 2002-164614 A | 6/2002 |

(Continued)

OTHER PUBLICATIONS

Eckstein et al., "High-Resolution Two-Photon Spectroscopy with Picosecond Light Pulses", Phys. Rev. Lett., vol. 40, 1978, pp. 847-850.

(Continued)

*Primary Examiner* — Tri T Ton
*Assistant Examiner* — Rufus L Phillips
(74) *Attorney, Agent, or Firm* — HoustonHogle LLP

(57) ABSTRACT

An optical coherence analysis system uses a laser swept source that is constrained to operate in a mode locked condition. This is accomplished by synchronously changing the laser cavity's gain and/or phase based on the round trip travel time of light in the cavity. Many high-speed wavelength swept laser sources emit pulses synchronized with the round trip time of the cavity as part of a nonlinear optical frequency red shifting process. Stable pulsation is associated with smooth tuning and low relative intensity noise. Addition of mode-locking methods to this class of lasers can control and stabilize these lasers to a low clock jitter and RIN state, and in specific cases allow long-to-short wavelength tuning in addition to the usual short-to-long (red (Continued)

shifting). The laser may comprise a SOA (410), a tunable Fabry-Perot-Filter (412) as one reflector and an Output coupler (405) in an optical fiber (406) to adjust the cavity length.

4 Claims, 23 Drawing Sheets

(51) Int. Cl.
| | |
|---|---|
| H01S 3/11 | (2006.01) |
| H01S 5/04 | (2006.01) |
| H01S 5/14 | (2006.01) |
| G01N 21/47 | (2006.01) |
| H01S 3/067 | (2006.01) |
| H01S 3/083 | (2006.01) |
| H01S 3/094 | (2006.01) |
| H01S 3/106 | (2006.01) |
| H01S 5/022 | (2006.01) |
| H01S 5/026 | (2006.01) |
| H01S 5/062 | (2006.01) |
| H01S 5/065 | (2006.01) |

(52) U.S. Cl.
CPC ..... *G01B 9/02004* (2013.01); *G01N 21/4795* (2013.01); *H01S 3/1112* (2013.01); *H01S 5/0657* (2013.01); *H01S 5/06216* (2013.01); *H01S 5/141* (2013.01); *H01L 2224/48091* (2013.01); *H01S 3/06791* (2013.01); *H01S 3/083* (2013.01); *H01S 3/094026* (2013.01); *H01S 3/1062* (2013.01); *H01S 3/1109* (2013.01); *H01S 3/1118* (2013.01); *H01S 5/0265* (2013.01); *H01S 5/02284* (2013.01); *H01S 5/041* (2013.01); *H01S 5/0622* (2013.01); *H01S 5/146* (2013.01)

(56) References Cited

U.S. PATENT DOCUMENTS

| | | | |
|---|---|---|---|
| 3,815,046 | A | 6/1974 | Johnson et al. |
| 4,081,765 | A | 3/1978 | Berg et al. |
| 4,918,396 | A | 4/1990 | Halemane et al. |
| 5,509,022 | A | 4/1996 | Lowery et al. |
| H1813 | H | 11/1999 | Kersey |
| 6,044,097 | A | 3/2000 | Kawamura et al. |
| 6,192,058 | B1 | 2/2001 | Abeles |
| 6,345,059 | B1 | 2/2002 | Flanders |
| 6,366,592 | B1 | 4/2002 | Flanders |
| 6,373,632 | B1 | 4/2002 | Flanders |
| 6,501,551 | B1 | 12/2002 | Tearney et al. |
| 6,608,711 | B2 | 8/2003 | Flanders et al. |
| 6,816,515 | B1 | 11/2004 | Yun et al. |
| 7,139,078 | B2 | 11/2006 | Hogan |
| 7,414,779 | B2 | 8/2008 | Huber et al. |
| 7,415,049 | B2 | 8/2008 | Flanders et al. |
| 7,701,982 | B2 | 4/2010 | Yu et al. |
| 7,733,923 | B2 | 6/2010 | Doerr |
| 7,813,388 | B2 | 10/2010 | Park et al. |
| 8,059,277 | B2 | 11/2011 | Atia et al. |
| 8,285,368 | B2 * | 10/2012 | Chen .................. A61B 5/0066 600/101 |
| 8,384,909 | B2 | 2/2013 | Yun et al. |
| 8,494,016 | B2 | 7/2013 | Karni et al. |
| 2002/0064353 | A1 | 5/2002 | Yokoyama |
| 2003/0179790 | A1 | 9/2003 | Bouda et al. |
| 2004/0100675 | A1 | 5/2004 | Matsko et al. |
| 2005/0018714 | A1 | 1/2005 | Fermann et al. |
| 2006/0109873 | A1 | 5/2006 | Crosson et al. |
| 2006/0187537 | A1 | 8/2006 | Huber et al. |
| 2007/0268939 | A1 | 11/2007 | Cattellan et al. |
| 2007/0297462 | A1 | 12/2007 | Jalali et al. |
| 2009/0059970 | A1 | 3/2009 | Atia et al. |
| 2009/0067456 | A1 | 3/2009 | Villeneuve et al. |
| 2009/0107962 | A1 | 4/2009 | Munroe et al. |
| 2009/0174931 | A1 | 7/2009 | Huber et al. |
| 2009/0290167 | A1 | 11/2009 | Flanders et al. |
| 2009/0310627 | A1 * | 12/2009 | Chen .................. H01S 5/146 372/6 |
| 2010/0210952 | A1 | 8/2010 | Taira et al. |
| 2011/0155916 | A1 | 6/2011 | Furusawa et al. |
| 2011/0216325 | A1 | 9/2011 | Schmitt |
| 2012/0162662 | A1 | 6/2012 | Johnson et al. |
| 2012/0219026 | A1 | 8/2012 | Saracco et al. |

FOREIGN PATENT DOCUMENTS

| | | |
|---|---|---|
| JP | 2007-229310 A | 9/2007 |
| JP | 2009-049123 A | 3/2009 |
| JP | WO2009133734 A1 | 5/2009 |
| JP | 2009-277754 A | 11/2009 |
| JP | 2010-010172 A | 1/2010 |
| JP | 2010225688 A | 10/2010 |
| JP | 2011-524003 A | 8/2011 |
| WO | 9956360 A1 | 11/1999 |
| WO | 2009/139481 A1 | 11/2009 |
| WO | 2010/111795 A1 | 10/2010 |

OTHER PUBLICATIONS

Bilenca, A. et al., "Numerical study of wavelength-swept semiconductor ring lasers: the role of refractive-index nonlinearities in semiconductor optical amplifiers and implications for biomedical imaging applications," Optics Letters, vol. 31, No. 6, Optical Society of America, Mar. 15, 2006, pp. 760-762.

Choma, M. et al., "Sensitivity advantage of swept source and Fourier domain optical coherence tomography," Optics Express, vol. 11, No. 18, Optical Society of America, Sep. 8, 2003, pp. 2183-2189.

Chong, C. et al., "Large coherence length swept source for axial length measurement of the eye," Applied Optics, vol. 48, No. 10, Optical Society of America, Apr. 1, 2009, pp. D144-D150.

Chong, C. et al., "Spectral narrowing effect by quasi-phase continuous tuning in high-speed wavelength-swept light source," Optics Express, vol. 16, No. 25, Optical Society of America, Dec. 8, 2008, pp. 21105-21118.

De Boer, J. et al., "Improved signal-to-noise ratio in spectral-domain compared with time-domain optical coherence tomography," Optics Letters, vol. 28, No. 21, Optical Society of America, Nov. 3, 2003, pp. 2067-2069.

Eigenwillig, C. et al., "K-space linear Fourier domain mode locked laser and applications for optical coherence tomography," Optics Express, vol. 16, No. 12, Optical Society of America, Jun. 9, 2008, pp. 8916-8937.

Goldberg, B. et al., "Miniature swept source for point of care Optical Frequency Domain Imaging," Optics Express, vol. 17, No. 5, Optical Society of America, Mar. 2, 2009, pp. 3619-3629.

Hee, M. et al., "Femtosecond transillumination optical coherence tomography," Optics Letters, vol. 18, No. 12, Jun. 15, 1993, pp. 950-952.

Huang, S. et al., "Swept source optical coherence microscopy using a Fourier domain mode-locked laser," Optics Express, vol. 15, No. 10, Optical Society of America, May 14, 2007, pp. 6210-6217.

Huber, R. et al., "Amplified, frequency swept lasers for frequency domain reflectometry and OCT imaging: design and scaling principles," Optics Express, vol. 13, No. 9, Optical Society of America, May 2, 2005, pp. 3513-3528.

Huber, R. et al., "Fourier Domain Mode Locking (FDML): A new laser operating regime and applications for optical coherence tomography," Optics Express, vol. 14, No. 8, Optical Society of America, Apr. 17, 2006, pp. 3225-3237.

Jenkins, M. et al., "Ultrahigh-speed optical coherence tomography imaging and visualization of the embryonic avian heart using a buffered Fourier Domain Mode Locked laser," Optics Express, vol. 15, No. 10, Optical Society of America, May 14, 2007, pp. 6251-6267.

(56) References Cited

OTHER PUBLICATIONS

Kuznetsov, M. et al., "Compact Ultrafast Reflective Fabry-Perot Tunable Lasers for OCT Imaging Applications," SPIE BiOS, RFPTL Lasers for OCT, Jan. 26, 2010, 21 pages.
Leitgeb, R. et al., "Performance of fourier domain vs. time domain optical coherence tomography," Optics Express, vol. 11, No. 8, Optical Society of America, Apr. 21, 2003, pp. 889-894.
Sutter, D. et al., "Semiconductor saturable-absorber mirror-assisted Kerr-lens mode-locked Ti:sapphire laser producing pulses in the two-cycle regime," Optics Letters, vol. 24, No. 9, Optical Society of America, May 1, 1999, pp. 631-633.
Yun, S. et al., "Extended-Cavity Semiconductor Wavelength-Swept Laser for Biomedical Imaging," IEEE Photonics Technology Letters, vol. 16, No. 1, Jan. 2004, pp. 293-295.
Yun, S. et al., "High-speed optical frequency-domain imaging," Optics Express, vol. 11, No. 22, Optical Society of America, Nov. 3, 2003, pp. 2953-2963.
Yun, S. et al., "High-speed wavelength-swept semiconductor laser with a polygon-scanner-based wavelength filter," Optics Letters, vol. 28, No. 20, Optical Society of America, Oct. 15, 2003, pp. 1981-1983.
Yun, S. et al., "Wavelength Swept Lasers," Optical Coherence Tomography, Springer-Verlag Berlin Heidelberg, 2008, pp. 359-377.
Kuznetsov, M. et al., "Compact Ultrafast Reflective Fabry-Perot Tunable Lasers for OCT Imaging Applications," Proceedings of the SPIE, vol. 7554, 2010, pp. 75541F-1 to 75541F-6.
International Search Report, dated Apr. 3, 2012, from International Application No. PCT/US2011/067413, filed on Dec. 27, 2011.
Braaf, Boy, et al., "Phase-stabilized optical frequency domain imaging at 1-μm for the measurement of blood flow in the human choroid," Optics Express, vol. 19, No. 22, pp. 20886-20903, Oct. 24, 2011.
Dhalla, Al-Hafeez, et al., "Complex conjugate resolved heterodyne swept source optical coherence tomography using coherence revival," Biomedical Optics Express, vol. 3, No. 3, pp. 633-649, Mar. 1, 2012.
Haus, Herman A., "Mode-Locking of Lasers," IEEE Journal on Selected Topics in Quantum Electronics, vol. 6, No. 6, pp. 1173-1185, Nov./Dec. 2000.
Kuznetsov, Mark, et al., "Compact Ultrafast Reflective Fabry-Perot Tunable Lasers for OCT Imaging Applications," Proc. of SPIE, vol. 7554, pp. 75541F-1 to 75541F-6, SPIE Photonics West Jan. 25-27, 2010.

Abedin, K. S. et al., "Beat-Spectrum Tailoring of Fiber Lasers Using an Intracavity Fabry-Perot Filter for Regenerative and Harmonic Mode-Locking," IEEE Photonics Technology Letters, vol. 11, No. 7, Jul. 1999, pp. 800-802.
Dhalla, Al-H. et al., "Complete complex conjugate resolved heterodyne swept-source optical coherence tomography using a dispersive optical delay line," Biomedical Optics Express, vol. 2, No. 5, Optical Society of America, Apr. 15, 2011, pp. 1218-1232.
Huo, L. et al., "Self-regenerative FDML for OCT imaging," presented at SPIE Photonics West—BiOS conference, Session 8. No. 7889-50., Jan. 25, 2011.
Kafka, J. D. et al., "Picosecond and Femtosecond Pulse Generation in a Regeneratively Mode-Locked Ti : Sapphire Laser," IEEE Journal of Quantum Electronics, vol. 28, No. 10, Oct. 1992, pp. 2151-2162.
Margalit, M. et al., "Harmonic Mode-Locking Using Regenerative Phase Modulation," IEEE Photonics Technology Letters, vol. 10, No. 3, Mar. 1998, pp. 337-339.
Murari, K. et al., "Self-starting, self-regulating Fourier domain mode locked fiber laser for OCT imaging," Biomedical Optics Express, vol. 2, No. 7, Optical Society of America, Jun. 22, 2011, pp. 2005-2011.
Nakazawa, M. et al., "Ultrastable harmonically and regeneratively modelocked polarisation-maintaining erbium fibre ring laser," Electronic Letters, vol. 30, No. 19, Sep. 15, 1994, pp. 1603-1605.
Tsuchida, H., "160-Gb/s Optical Clock Recovery Using a Regeneratively Mode-Locked Laser Diode," IEEE Photonics Technology Letters, vol. 18, No. 16, Aug. 15, 2006, pp. 1687-168.
Yan, C. et al., "Picosecond Semiconductor Lasers Based on Regenerative Feedback Schemes," Center for High Technology Materials, The University of New Mexico, Albuquerque, NM 87131, pp. 286-289.
Yun, S. et al., "Removing the depth-degeneracy in optical frequency domain imaging with frequency shifting," Optics Express, vol. 12, No. 20., Optical Society America, Oct. 4, 2004, pp. 4822-4828.
Avrutin, Eugene A., et al., "Travelling wave modeling and dynamic properties of short external cavity semiconductor lasers with fast intracavity frequency sweeping for biomedical imaging applications," Dept. of Electronics, University of York, York Y0105DD, UK, Submitted to the IEEE Journal of Selected Topics in Quantum Electronics, JSTQE 2013, pp. 1-8.
International Preliminary Report on Patentability and the Written Opinion of the International Searching Authority dated Jul. 11, 2013, from counterpart International Application No. PCT/US2011/067413, filed on Dec. 27, 2011.
Wang, F. et al., "Wideband-tuneable, nanotube mode-locked, fibre laser," Nature Nanotechnology, vol. 3, Macmillan Publishers Limited, Dec. 2008, pp. 738-742.

\* cited by examiner

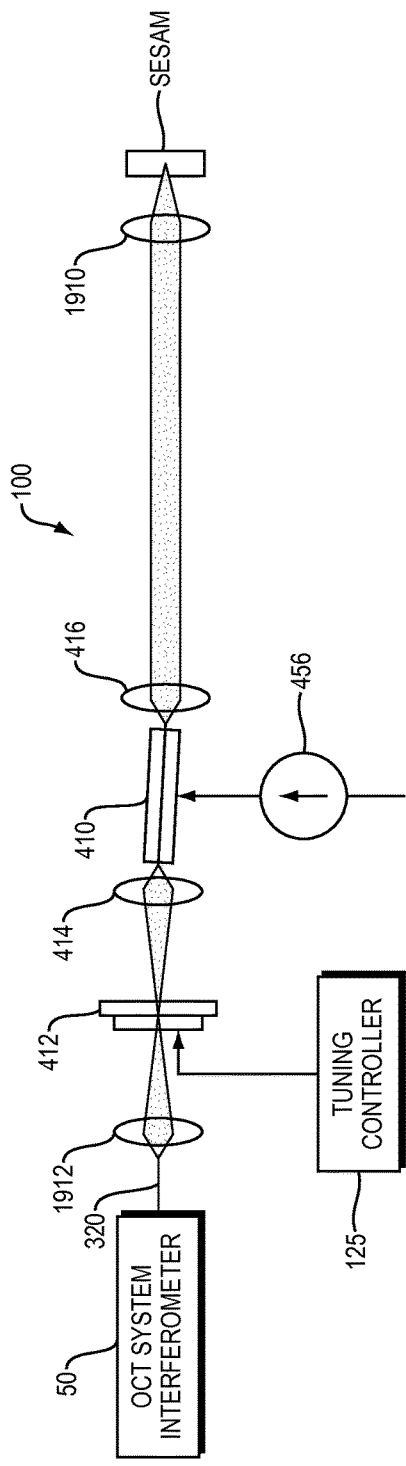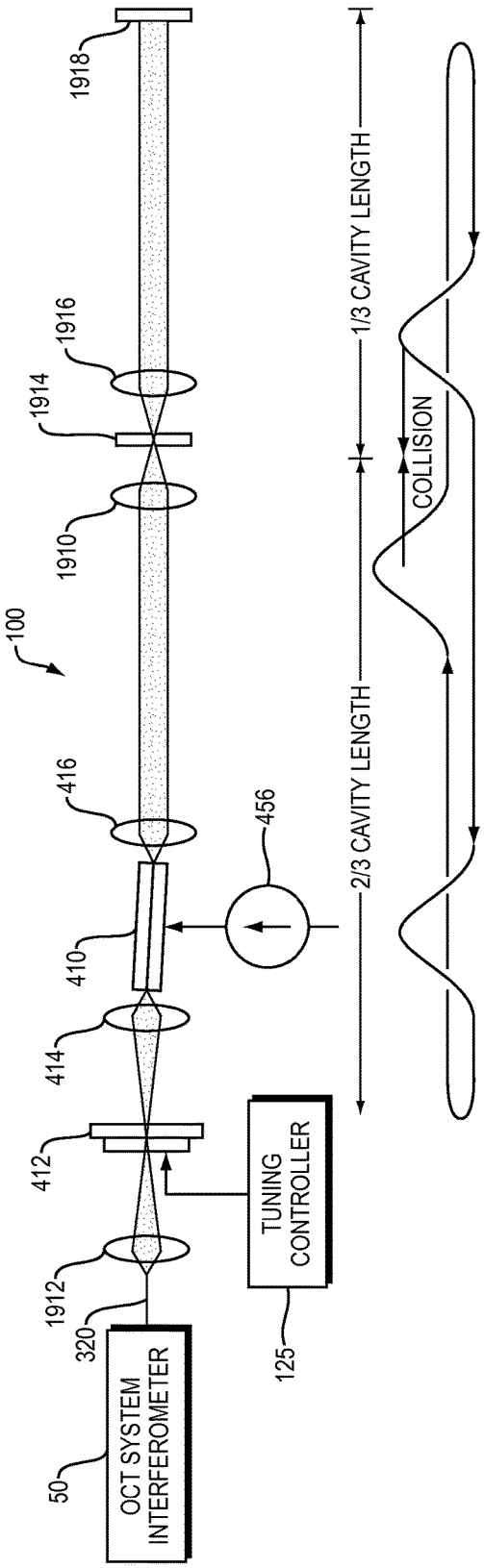
FIG. 19
FIG. 20

LASER SWEPT SOURCE WITH CONTROLLED MODE LOCKING FOR OCT MEDICAL IMAGING

RELATED APPLICATIONS

This application claims priority to U.S. patent application Ser. No. 12/979,225, filed on Dec. 27, 2010, which is incorporated herein by reference in its entirety.

BACKGROUND OF THE INVENTION

Optical coherence analysis relies on the use of the interference phenomena between a reference wave and an experimental wave or between two parts of an experimental wave to measure distances and thicknesses, and calculate indices of refraction of a sample. Optical Coherence Tomography (OCT) is one example technology that is used to perform high-resolution cross sectional imaging. It is often applied to imaging biological tissue structures, for example, on microscopic scales in real time. Optical waves are reflected from an object or sample and a computer produces images of cross sections of the object by using information on how the waves are changed upon reflection.

Fourier domain OCT (FD-OCT) currently offers the best performance for many applications. Moreover, of the Fourier domain approaches, swept-source OCT has distinct advantages over techniques such as spectrum-encoded OCT because it has the capability of balanced and polarization diversity detection. It has advantages as well for imaging in wavelength regions where inexpensive and fast detector arrays, which are typically required for spectrum-encoded FD-OCT, are not available.

In swept source OCT, the spectral components are not encoded by spatial separation, but they are encoded in time. The spectrum is either filtered or generated in successive frequency steps and reconstructed before Fourier-transformation. Using the frequency scanning swept source, the optical configuration becomes less complex but the critical performance characteristics now reside in the source and especially its frequency tuning speed and accuracy.

High speed frequency tuning for OCT swept sources is especially relevant to in vivo imaging where fast imaging reduces motion-induced artifacts and reduces the length of the patient procedure. It can also be used to improve resolution.

The swept sources for OCT systems have typically been tunable lasers. The advantages of tunable lasers include high spectral brightness and relatively simple optical designs. A tunable laser is constructed from a gain medium, such as a semiconductor optical amplifier (SOA) that is located within a resonant cavity, and a tunable element such as a rotating grating, grating with a rotating mirror, or a Fabry-Perot tunable filter. Currently, some of the highest tuning speed lasers are based on the laser designs described in U.S. Pat. No. 7,415,049 B1, entitled Laser with Tilted Multi Spatial Mode Resonator Tuning Element, by D. Flanders, M. Kuznetsov and W. Atia. The use of micro-electro-mechanical system (MEMS) Fabry-Perot tunable filters combines the capability for wide spectral scan bands with the low mass, high mechanical resonant frequency deflectable MEMS membranes that have the capacity for high speed tuning.

Certain tradeoffs in laser design, however, can be problematic for OCT systems. Generally, shorter laser cavities translate to higher potential tuning speeds, since laser oscillation must build up anew from spontaneous emission when the laser is tuned. Thus, round-trip travel time for the light in the laser cavities should be kept low so that this build up occurs quickly. Short laser cavities, however, create problems in terms of the spectral spacing of the longitudinal cavity modes of the laser. That is, lasers can only produce light at integer multiples of the cavity mode spacing since the light must oscillate within the cavities. Shorter cavities result in fewer and more widely spaced modes. This results in greater mode hopping noise as the laser is tuned over these discrete cavity modes. So, when designing an OCT laser, there is typically a need to choose between low noise and high speed.

One laser design seeks to address this drawback. A Fourier-domain mode-locked laser (FDML) stores light in a long length of fiber for amplification and recirculation in synchronism with the laser's tuning element. See "Fourier Domain Mode Locking (FDML): A new laser operating regime and applications for optical coherence tomography", R. Huber, M. Wojtkowski, and J. G. Fujimoto, 17 Apr. 2006/Vol. 14, No. 8/OPTICS EXPRESS 3225. The drawback of these devices is their complexity, however. Moreover, the ring cavity including the long storage fiber creates its own performance problems such as dispersion and stability.

SUMMARY OF THE INVENTION

Research with tunable lasers has shown that when they are operated at high swept rates they tend to operate in a mode locked regime. At high sweep rates, one or more pulses travel in the laser cavity as is found in a traditional mode locked laser. The pulse repetition rate is close to the laser cavity roundtrip time or to a typically small, say a factor of 2 to 10, multiple. Since this mode locking rises from frequency tuning of the laser, it is termed swept mode locking. This mode locked regime can have the effect of actually facilitating the high-speed tuning of the laser. A four-wave mixing effect red shifts the wave in the laser cavity. This facilitates the tuning to lower optical frequencies. See A. Bilenca, S. H. Yun, G. J. Tearney, and B. E. Bouma, "Numerical study of wavelength-swept semiconductor ring lasers: the role of refractive-index nonlinearities in semiconductor optical amplifiers and implications for biomedical imaging applications", OPTICS LETTERS/Vol. 31, No. 6/Mar. 15, 2006.

Problems, however, arise when tuning to higher optical frequencies. Other problems arise because the laser cavity is changing through the process of tuning, and thus the characteristics that instigate the swept mode locking also change. As a result, the lasers can flip to other swept mode locked regimes during a single frequency scan of the tunable laser. For example, during the sweep, the number of pulses circulating in the cavity can change. As a result, the lasers can behave chaotically and unpredictably as they move between the different regimes, and the different regimes can result in different performance characteristics as the tunable lasers relate to the OCT systems in which they operate.

The present invention concerns a swept tunable laser source. During its swept operation, it is constrained to operate in a stable mode locked regime. In the illustrated embodiments, this is accomplished by actively modulating cavity gain and/or intracavity elements or including active or passive elements that will facilitate stable operation during the scan. This has the effect of stabilizing the emission characteristics of the laser and avoids noisy disruptions due to uncertainty or flips in the number of pulses circulating in the cavity. Instead, the mode locking system stabilizes the pulsation behavior of the laser by modulating a gain, for example, of the cavity of the laser at a harmonic of the cavity round trip frequency. In other embodiments described below, the stabilization is accomplished by modulating an intracavity phase modulator or a lossy element within the cavity. In still other embodiments, stabilization is facilitated with an intracavity saturable absorber, for example. As a result, in some cases operation in a stable mode locked regime can facilitate not only the tuning to lower optical frequencies, but also high speed tuning to higher optical frequencies to thereby enable stable and smooth up and down tuning.

More specifically, useful mode-locking methods include active gain modulation through current injection or synchronous pumping, active loss modulation, active phase modulation and passive mode locking Active phase modulation allows for both short-to-long and long-to-short tuning directions. Gated mode locking can be used to select one pulse per round trip in cases where the laser naturally emits more than one.

In general, according to one aspect, the invention features an optical coherence imaging method. The method comprises providing a laser swept source, controlling a mode-locked operation of laser swept source and generating a swept optical signal, transmitting the swept optical signal to an interferometer having a reference arm and a sample arm, in which a sample is located, combining the swept optical signal returning from the sample arm and the reference arm to generate an interference signal, detecting the interference signal, and generating image information of the sample from the detected interference signal.

In one embodiment, the mode-locked operation of the laser swept source is controlled by controlling a bias current to an optical gain element that amplifies light in a laser cavity of the laser swept source. The bias current is preferably modulated at a frequency based on a roundtrip travel time of light in the laser cavity.

More generally, in many embodiments, the mode-locked operation of the laser swept source is controlled by modulating a gain of a laser cavity of the laser swept source.

In other embodiments, controlling the mode-locked operation of the laser swept source comprises modulating phase of optical signals in the laser cavity.

In some embodiments, gated mode locking is implemented in which the number of pulses circulating in the laser cavity is reduced.

In general, according to another aspect, the invention features an optical coherence analysis system comprising a swept laser source for generating a swept optical signal that is frequency tuned over a tuning band, in which a mode-locked operation of the swept laser source is controlled, an interferometer for dividing the swept optical signal between a reference arm and a sample arm leading to a sample, and a detector system for detecting an interference signal generated from the swept optical signal from the reference arm and from the sample arm.

In embodiments, the mode locked operation is controlled by phase modulators and/or modulating a gain of the laser cavity. The modulation is preferably based on the roundtrip travel time of light in the cavity.

In general, according to another aspect, the invention features a mode-locked swept laser source, comprising a gain element in a laser cavity for amplifying light, a tunable element for the laser cavity, and a tuning controller for sweeping the tunable element over a tuning band to generate a swept optical signal. According to the invention, a mode-locked operation of swept laser source is controlled.

In other examples, the mode locking system comprises a phase modulator or a loss modulator in the cavity or gain modulation by synchronous optical pumping. Another system adds a saturable absorber to the cavity to stabilize swept mode locking using passive mode locking methods.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same or similar parts throughout the different views. The drawings are not necessarily to scale; emphasis has instead been placed upon illustrating the principles of the invention. Of the drawings:

FIG. 19 is a schematic diagram showing a linear cavity mode-locked laser swept source for optical coherence analysis using a saturable absorber mirror to control the mode-locked operation;

FIG. 20 is a schematic diagram showing a linear cavity mode-locked laser swept source for optical coherence analysis using a transmissive saturable absorber to control the mode-locked operation.

DETAILED DESCRIPTION OF THE PREFERRED EMBODIMENTS

Figure 1:
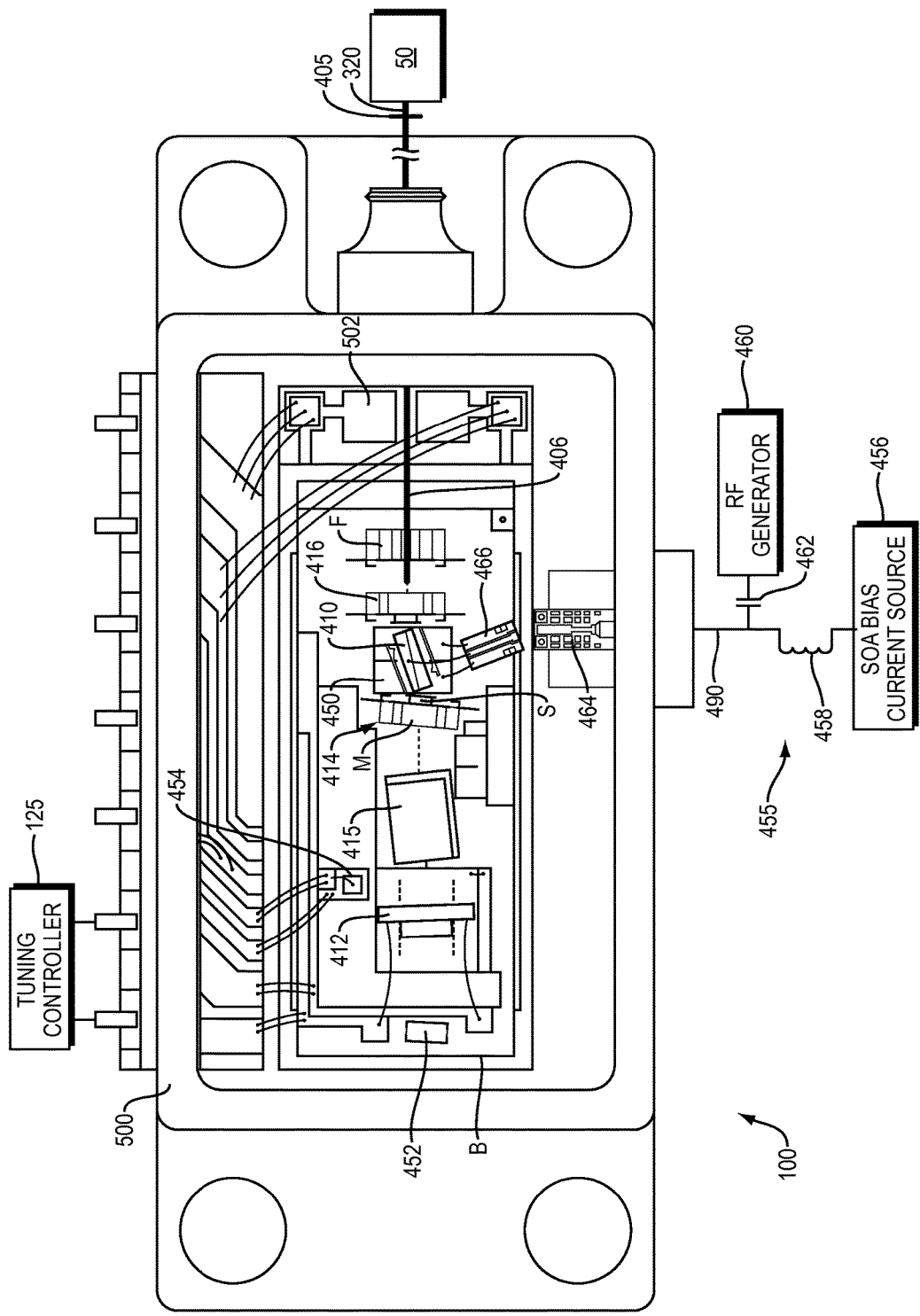
FIG. 1 is a top plan scale drawing of the mode-locked laser swept source for optical coherence analysis according to a first embodiment the present invention.

FIG. 1 shows mode-locked laser swept source 100 for optical coherence analysis, which has been constructed according to the principles of the present invention. This embodiment controls or stabilizes the mode-locked operation by modulating the bias current to an intracavity gain element.

In the current embodiment, the laser swept source 100 is preferably a laser as generally described in incorporated U.S. Pat. No. 7,415,049 B1. It includes a linear cavity with a gain element 410 and a frequency tuning element 412. In the illustrated example, the frequency tuning element is a Fabry-Perot filter, which defines one end of the cavity, in the illustrated implementation.

In other embodiments, other cavity configurations are used such as ring cavities. Further other cavity tuning elements are used such as gratings and thin-film filters. These elements can also be located entirely within the cavity such as an angle isolated Fabry-Perot tunable filter or grating.

Currently, the passband of the Fabry-Perot filter 412 is between 1 and 10 GHz.

In more detail with respect to the current embodiment, the tunable laser 100 comprises a semiconductor gain chip 410 that is paired with a micro-electro-mechanical (MEMS) angled reflective Fabry-Perot tunable filter 412, which defines one end of the laser cavity. The cavity extends to a second output reflector 405 that is located at the end of a fiber pigtail 406 that is coupled to the bench and also forms part of the cavity.

Currently, the length of the cavity is at least 40 millimeters (mm) long and preferably over 50 to 80 mm. This ensures close longitudinal mode spacing that reduces mode hopping noise.

In other embodiments, shorter cavities are used. In some embodiments, very short cavities with wider passband tuning elements (filters) 412 are used for extremely high speed applications where only short coherence lengths are required. In some of these examples, the passband of the Fabry-Perot filter 412 is between 20 and 40 GHz, or wider.

Nevertheless, the length of the cavity in any of these embodiments is relatively short when compared with FDML lasers. The cavity lengths in FDML lasers tend to be in the kilometer range. In contrast, almost all of the embodiments of the present laser have cavities of less than a meter long.

The tunable or swept optical signal passing through the output reflector 405 is transmitted on optical fiber 320 or via free space to an interferometer 50 of the OCT system.

The semiconductor optical amplifier (SOA) chip gain element 410 is located within the laser cavity. In the current embodiment, input and output facets of the SOA chip 410 are angled and anti-reflection (AR) coated, providing parallel beams from the two facets. In the preferred embodiment, the SOA chip 410 is bonded or attached to the common bench B via a submount 450.

The material system of the chip 410 is selected based on the desired spectral operating range. Common material systems are based on III-V semiconductor materials, including binary materials, such as GaN, GaAs, InP, GaSb, InAs, as well as ternary, quaternary, and pentenary alloys, such as InGaN, InAlGaN, InGaP, AlGaAs, InGaAs, GaInNAs, GaInNAsSb, AlInGaAs, InGaAsP, AlGaAsSb, AlGaInAsSb, AlAsSb, InGaSb, InAsSb, and InGaAsSb. Collectively, these material systems support operating wavelengths from about 400 nanometers (nm) to 2000 nm, including longer wavelength ranges extending into multiple micrometer wavelengths. Semiconductor quantum well and quantum dot gain regions are typically used to obtain especially wide gain and spectral emission bandwidths. Currently, edge-emitting chips are used although vertical cavity surface emitting laser (VCSEL) chips are used in different implementations.

The use of a semiconductor chip gain medium 410 has advantages in terms of system integration since semiconductor chips can be bonded to submounts that in turn are directly bonded to the bench B. Other possible gain media can be used in other implementations, however. Such examples include solid state gain media, such as rare-earth (e.g., Yb, Er, Tm) doped bulk glass, waveguides or optical fiber.

Each facet of the SOA 410 has an associated lens structure 414, 416 that is used to couple the light exiting from either facet of the SOA 410. The first lens structure 414 couples the light between the back facet of the SOA 410 and the reflective Fabry-Perot tunable filter 412. Light exiting out the output or front facet of the SOA 410 is coupled by the second lens structure 416 to a fiber end facet of the pigtail 406.

Each lens structure comprises a LIGA mounting structure M, which is deformable to enable post installation alignment, and a transmissive substrate S on which the lens is formed. The transmissive substrate S is typically solder or thermocompression bonded to the mounting structure M, which in turn is solder bonded to the optical bench B.

The fiber facet of the pigtail 406 is also preferably mounted to the bench B via a fiber mounting structure F, to which the fiber 406 is solder bonded. The fiber mounting structure F is likewise usually solder bonded to the bench B.

The angled reflective Fabry-Perot filter 412 is a multi-spatial-mode tunable filter that provides angular dependent reflective spectral response back into the laser cavity. This characteristic is discussed in more detail in incorporated U.S. Pat. No. 7,415,049 B1.

Preferably, the tunable filter 412 is a Fabry-Perot tunable filter that is fabricated using micro-electro-mechanical systems (MEMS) technology and is attached, such as directly solder bonded, to the bench B. Currently, the filter 412 is manufactured as described in U.S. Pat. No. 6,608,711 or 6,373,632, which are incorporated herein by this reference. A curved-flat resonator structure is used in which a generally flat mirror and an opposed curved mirror define a filter optical cavity, the optical length of which is modulated by electrostatic deflection of at least one of the mirrors.

Any light transmitted through the tunable filter 412 is directed to a beam dump component 452 that absorbs the light and prevents parasitic reflections in the hermetic package 500. In other examples, the transmitted light is provided to a k-clock subsystem as disclosed in U.S. Pat. Appl. Publ. No. 2009/0290167 A1, which is incorporated herein by this reference in its entirety.

The mode-locked laser swept source 100 and the other embodiments discussed hereinbelow are generally intended for high speed tuning to generate tunable optical signals that scan over the scanband at speeds greater than 1 kiloHertz (kHz). In current embodiments, the mode-locked laser swept source 100 tunes at speeds greater than 50 or 100 kHz. In very high speed embodiments, the mode-locked laser swept source 100 tunes at speeds greater than 200 or 500 kHz.

The tuning controller 125 provides a tuning voltage function to the Fabry-Perot filter 412 that sweeps the passband optical frequency across the tuning band, preferably with optical frequency varying linearly with time. Typically, the width of the tuning band is greater than 10 nm. In the current embodiments, it is preferably between 50 and 150 nm, although even wider tuning bands are contemplated some examples.

The tuning speed provided by the tuning controller 125 is also expressed in wavelength per unit time. In one example, for an approximately 110 nm tuning band or range or scan band and 100 kHz scan rate, assuming 60% duty cycle for substantially linear up-tuning, the peak sweep speed would be 110 nm*100 kHz/0.60=18,300 nm/msec=18.3 nm/μsec or faster. In another example, for an approximately 90 nm tuning range and 50 kHz scan rate, assuming a 50% duty cycle for substantially linear up-tuning, the peak sweep speed is 90 nm*50 kHz/0.50=9,000 nm/msec=9.0 nm/μsec or faster. In a smaller scan band example having an approximately 30 nm tuning range and 2 kHz scan rate, assuming a 80% duty cycle for substantially linear tuning, the peak sweep speed would be 30 nm*2 kHz/0.80=75 nm/msec=0.075 nm/μsec, or faster.

Thus, in terms of scan rates, in the preferred embodiments described herein, the sweep speeds are greater than 0.05 nm/μsec, and preferably greater than 5 nm/μsec. In still higher speed applications, the scan rates are higher than 10 nm/μsec.

In one implementation, an extender element 415 is added to the laser cavity. This is fabricated from a transparent, preferably high refractive index material, such as fused silica, silicon, GaP or other transmissive material having a refractive index of ideally about 1.5 or higher. Currently silicon or GaP is preferred. Both endfaces of the extender element 415 are antireflection coated. Further, the element 415 is preferably angled by between 1 and 10 degrees relative to the optical axis of the cavity to further spoil any reflections from the endfaces from entering into the laser beam optical axis.

The extender element 415 is used to change the optical distance between the laser intracavity spurious reflectors and thus change the depth position of the spurious peaks in the image while not necessitating a change in the physical distance between the elements.

The bench B is termed a micro-optical bench and is preferably less than 10 millimeters (mm) in width and about 25 mm in length or less. This size enables the bench to be installed in a standard, or near standard-sized, butterfly or DIP (dual inline pin) hermetic package 500. In one implementation, the bench B is fabricated from aluminum nitride. A thermoelectric cooler 502 is disposed between the bench B and the package 500 (attached/solder bonded both to the backside of the bench and inner bottom panel of the package) to control the temperature of the bench B. The bench temperature is detected via a thermistor 454 installed on the bench B.

The mode locking system of the illustrated embodiment includes a bias current modulation system 455. In more detail, a laser bias current source 456 supplies a direct current for the bias current supplied to the SOA 410. This current passes through an inductor 458. A radio frequency generator 460 generates an electronic signal having a frequency of a harmonic of the cavity round trip frequency. This frequency corresponds to the time required for light to make a round trip in the cavity of the laser 100. In the illustrated laser, this corresponds to twice the time required for light to propagate from the tunable filter 412 at one end of the cavity to the output reflector 405 at the end of the pigtail 406.

The signal from the RF generator is supplied through a capacitor 462 such that the capacitor 462 in combination with the inductor 458 yield a modulated bias current 490 that is delivered to the SOA 410 via a package impedance-matched stripline 464 and a bench-mounted impedance-matched stripline 466.

One difference between FDMLs and the swept mode locked lasers described here is how the mode locking is performed. For an FDML, the laser wavelength periodic sweep rate, given by the tunable filter sweep rate, is equal to the laser cavity roundtrip rate or its multiple, say a factor of 2 to 10 multiple. For 100 kHz typical sweep rate this requires kilometer or more long optical laser cavities. In contrast, for these relatively short-cavity OCT swept-mode locked lasers, the laser periodic wavelength sweep rate, e.g. 20-100 kHz, which is also given by the tunable filter sweep rate, is several orders of magnitude smaller than the laser cavity roundtrip rate, which is, for example, in the 1-3 GHz range. Here, wavelength sweep rate is very much smaller, by several orders of magnitude, than the laser cavity roundtrip rate, where for FDML the two rates are equal or a small multiple of each other.

Figure 2:
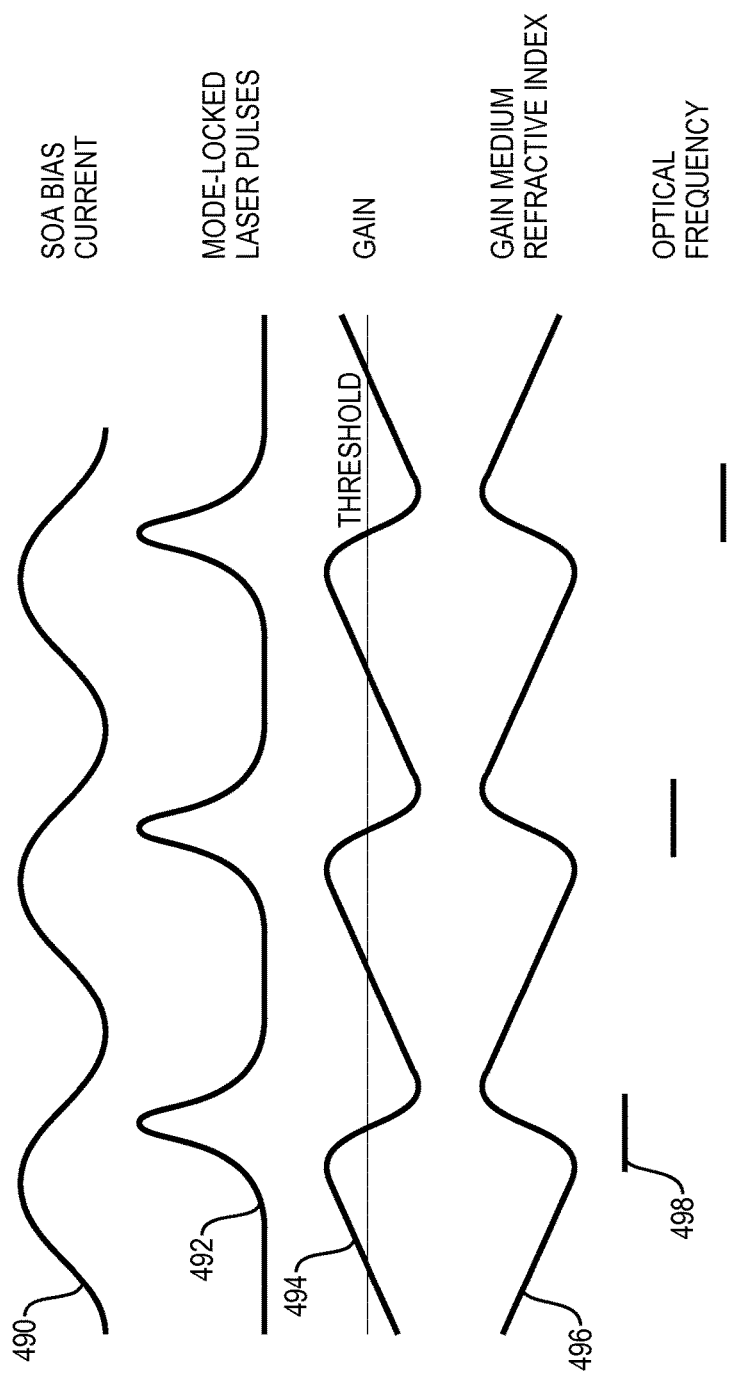
FIG. 2 is a plot of the modulated signal (e.g., SOA bias current) of the mode locking system, the laser pulses circulating in the laser cavity, the gain of the semiconductor gain medium (SOA), and the gain medium's refractive index as a function of time.

FIG. 2 illustrates the operation of the mode-locked laser swept source 100 and the four wave mixing process that facilitates its tuning to the lower optical frequencies. The purpose of this diagram is to describe, in a physical way, the red-shift mechanism in the four-wave-mixing process.

In more detail, a modulated bias is delivered to the SOA 410 in order to modulate the gain of the laser cavity. In the illustrated example, the bias current is generally sinusoidal, in one implementation. The frequency of the bias current is tuned to the round-trip travel time of light in the cavity of the laser 100, or a harmonic of that round-trip travel time. This bias current modulation constrains the laser 102 operate in a mode locked regime and controls the number of pulses, typically one or more pulses 492, that circulate in the laser's cavity. When a light pulse 492 passes through the semiconductor diode gain medium, it depletes the gain 494, and the gain recovers through current injection between pulses. The gain modulation is accompanied by a modulation in the real part of the refractive index 496. The power gain (g) (in 1/length units) is linked to the index (n) through the linewidth enhancement factor α:

$$\Delta n = -\alpha \frac{\lambda}{4\pi} \Delta g$$

The optical length of the chip increases while the pulse is passing through, which red shifts the pulse in a process similar to a Doppler shift.

Since α is positive for most semiconductor lasers, the optical frequency shift per round trip is negative. The wavelength is red shifted yielding a decrease in the optical frequency 498.

The mode locking system generates the modulated bias current signal 490 that constrains the tunable laser 100 to operate in the mode locked condition. Specifically, the cavity's gain is modulated synchronously with the mode-locked laser pulses 492 traveling in the cavity of the laser 100. This prevents chaotic pulsation and cleans up the clock jitter and relative intensity noise (RIN).

In other embodiments, the mode locking system is driven with more complex waveforms (non-sinusoids) synchronized to the round trip of the cavity. This may permit both blue and red shifting of pulses to either change the tuning direction or to reduce the tuning rate by red shifting some pulses and blue shifting others to reduce the overall tuning rate.

Figure 3:
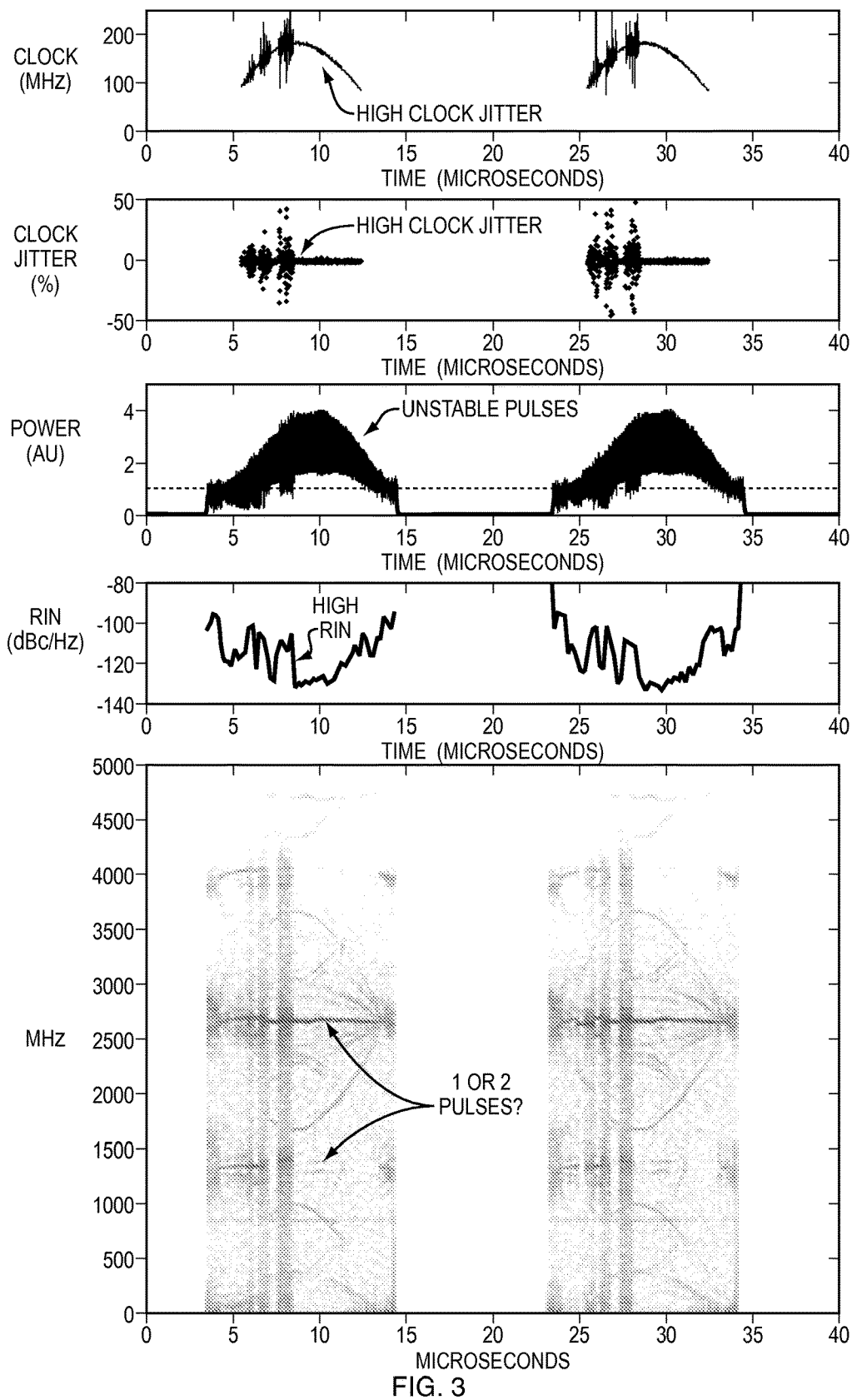
FIG. 3 contains five plots of experimental data on a common timescale in microseconds: clock frequency in MegaHertz, clock jitter in percent, laser power output in arbitrary units, relative intensity noise (RIN) (dBc/Hz), and a spectrogram showing the frequency content vs. time of the laser's instantaneous power output, illustrating a tunable laser source exhibiting swept mode locking during scanning over the tuning band but without any stabilization.

FIG. 3 contains plots of the k-clock frequency and clock jitter of the swept optical signal for the case where there is no active modulation of the SOA current. The k-clock exhibit high levels of jitter suggesting poor tuning performance. Further, the power output of the swept optical signal from tunable laser is highly unstable over the scan. RIN is also high. The spectrogram shows the existence of pulses in the swept optical signal at approximately 2600 and 1300 MHz. The energy distribution seems to vary over the course of the scan through the tuning band of the laser.

Figure 4:
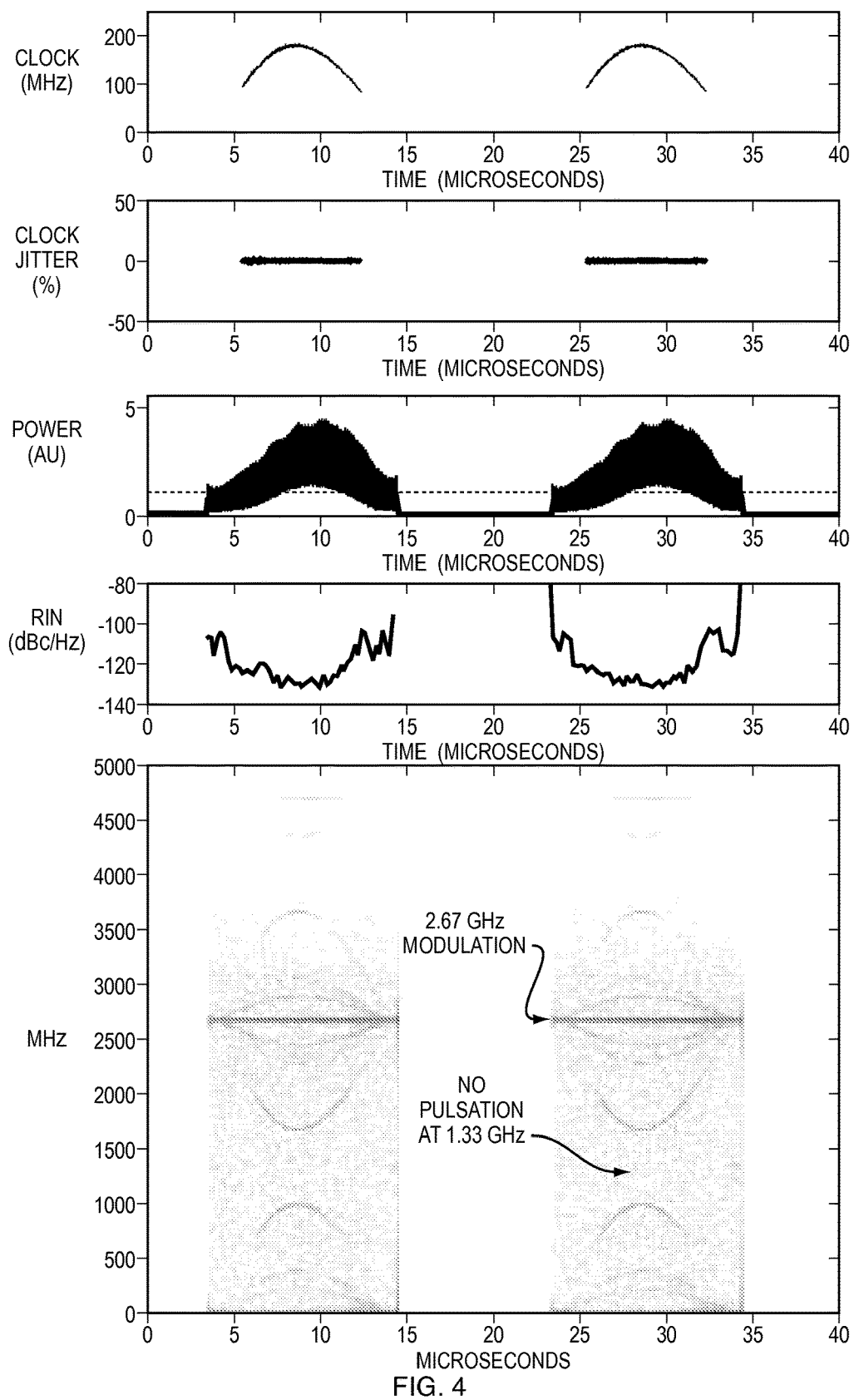
FIG. 4 contains five plots of experimental data on a common timescale in microseconds: clock frequency in megahertz, clock jitter in percent, laser power output in arbitrary units, relative intensity noise (RIN) (dBc/Hz), and a spectrogram showing the frequency content vs. time of the laser's instantaneous power output, illustrating the performance improvements of the tunable laser source when stabilization is added.

FIG. 4 illustrates the same the plots, but with the laser actively mode locked by applying 2600 MHz modulation to the SOA bias current. Here the k-clock frequency and clock jitter exhibit reduced jitter for the swept optical signal. Further, the power is more consistent during the tuning over the band, and RIN is lower. Further, with reference to the spectrogram of the swept optical signal, there is no pulsation at 1300 MHz, but only at 2600 MHz, suggesting that the laser is operating in a stable fashion with two pulses circulating within the cavity.

Figure 5A:
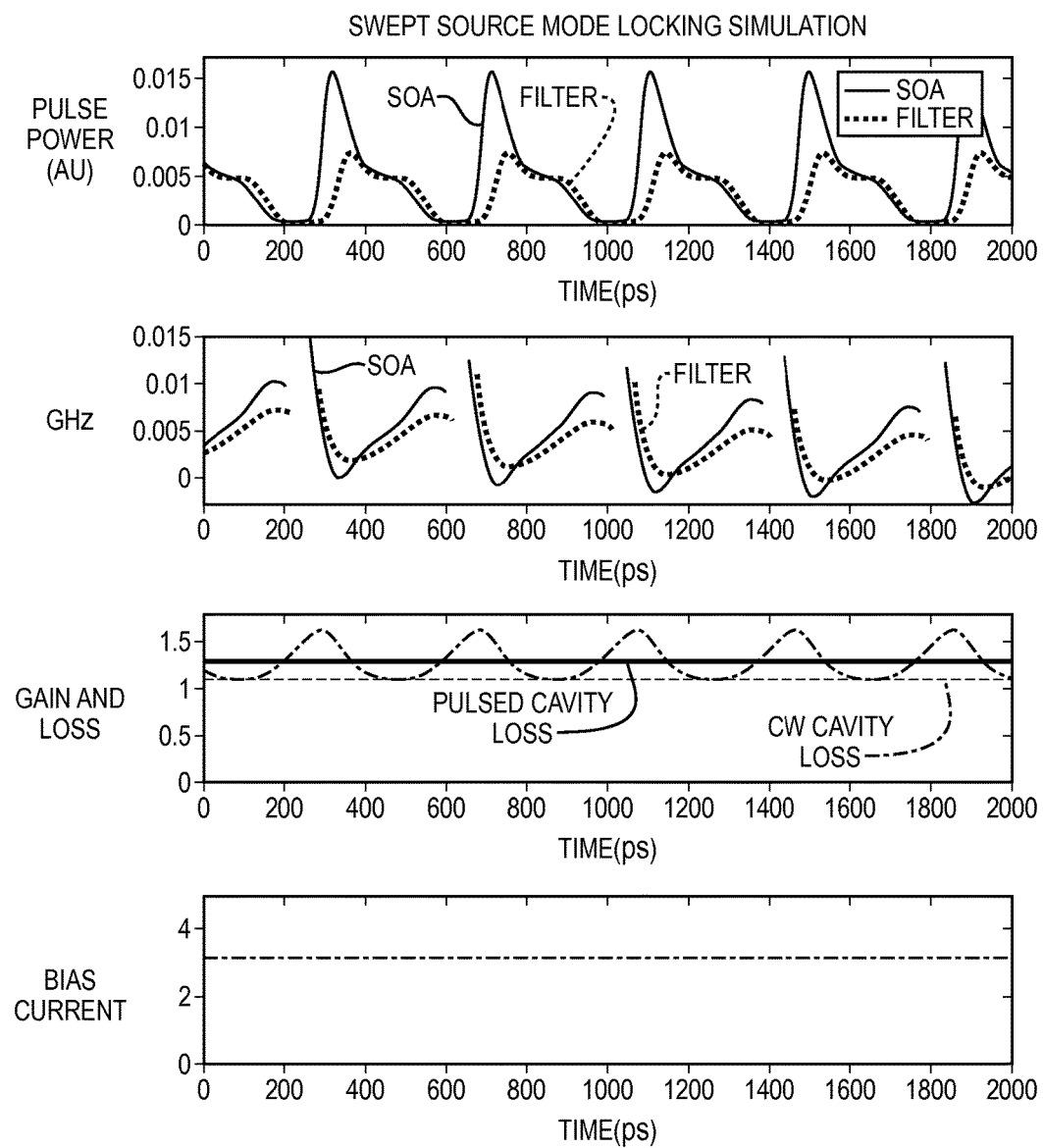
FIG. 5A contains four plots from a computer simulation on a common timescale in picoseconds: optical power for light exiting the SOA 410 and the Fabry-Perot tunable filter 412, the instantaneous optical frequency change of the pulses in GigaHertz (GHz), the gain from the SOA 410, and the bias current to the SOA 410.
Figure 5B:
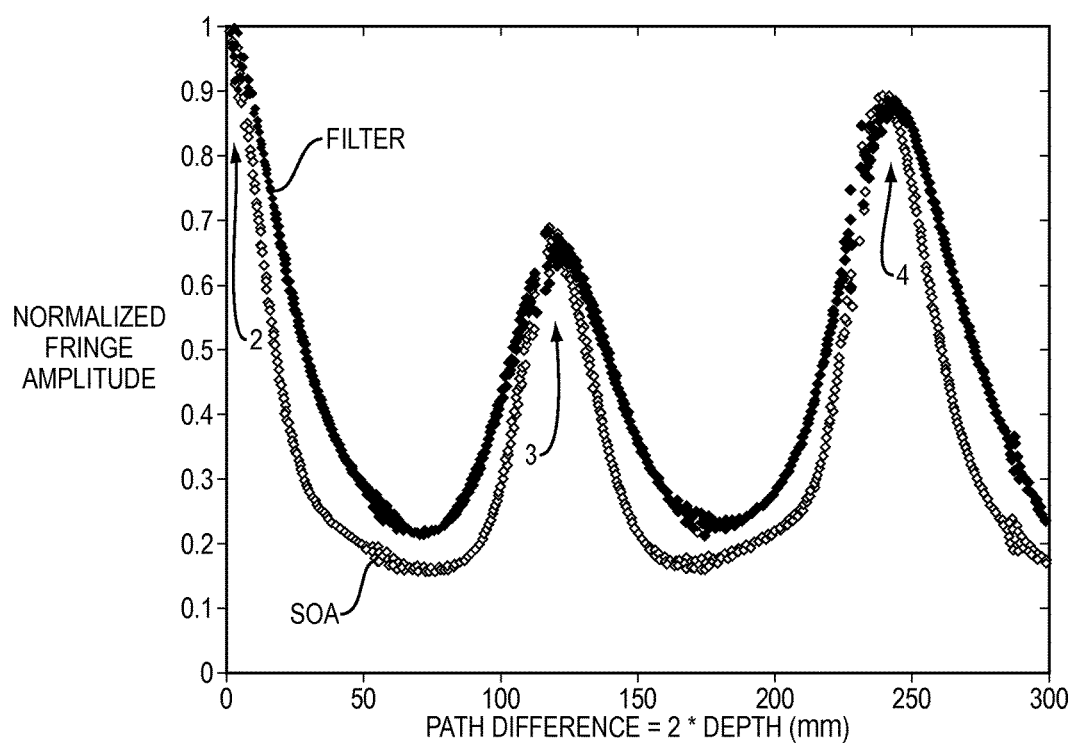
FIG. 5B is a plot of normalized fringe amplitude from a test interferometer as a function of depth in millimeters, illustrating a tunable laser source exhibiting swept mode locking during scanning over the tuning band but without any stabilization.

FIGS. 5A and 5B are the results of a computer simulation. It shows a tunable laser exhibiting swept mode locking without gain modulation. In this case, the laser operates with 2 pulses per cavity round trip.

The correlation plots of FIG. 5B, one for light exiting the SOA 410 and one for light exiting the tunable filter 412, are computer simulations of a swept source coherence length measurement, but carried out to extreme path differences. The usual coherence length measurement occurs at path differences near zero (2). At 120 mm (3) the pulses are interfering with their neighbors. At 240 mm (4) the pulses are interfering with pulses 1 cavity round trip away, which is two pulses apart.

Figure 6A:
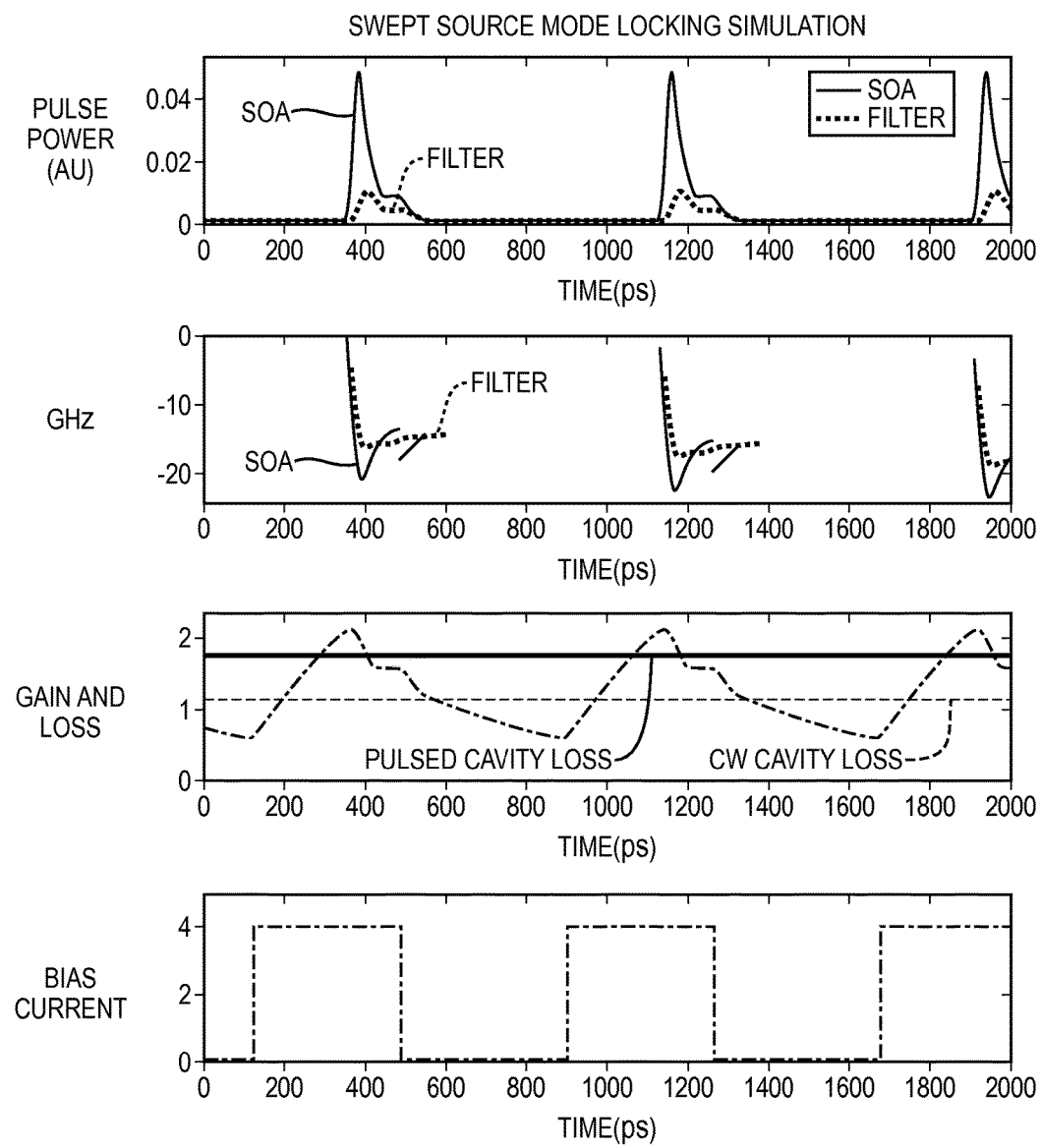
FIG. 6A contains four plots from a computer simulation on a common timescale in picoseconds: optical power for light exiting the SOA 410 and the Fabry-Perot tunable filter 412, the instantaneous optical frequency change in GigaHertz (GHz), the gain from the SOA 410, and the bias current to the SOA 410.
Figure 6B:
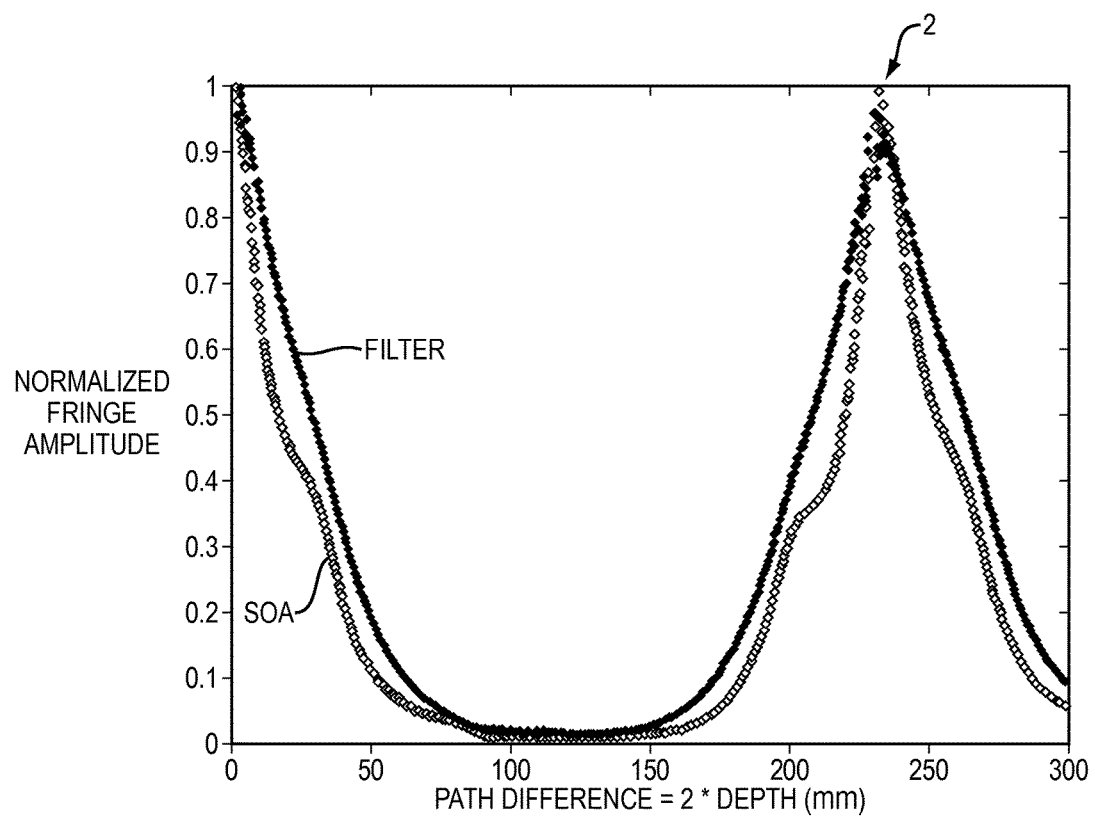
FIG. 6B is a plot of normalized fringe amplitude from a test interferometer as a function of depth in millimeters, illustrating the performance of a tunable laser with stabilized mode locking during scanning over the tuning band in which only one pulse is allowed to circulate within the laser cavity by application of a square wave SOA bias current to thereby implement active gated swept mode locking.

These secondary coherences (3) (4) can sometimes be a problem in practical OCT systems where small stray reflections at lengths nearly corresponding to the cavity length or fractions thereof (depending on the number of pulses per round trip) can produce artifacts in the OCT image. It is helpful to eliminate these as much as possible. FIGS. 6A and 6B are the results of another computer simulation. It shows a tunable laser with stabilized swept mode locking. In this case, the laser is constrained to operate with only 1 pulse per cavity round trip, termed gated swept mode locking.

Gated mode locking is used in some examples to increase the spacing between "coherence repeats" that can cause image artifacts in practical OCT systems.

The swept optical signal from the laser 100 has repeated coherence peaks at the pulse spacing. If the laser is normally harmonically mode locked, the pulse spacing is increased by gated mode locking, where the gain is modulated at the round-trip time of the cavity, rather than at a harmonic, or at a lower harmonic than its typical pulse spacing.

The "gated" mode locking is effected by applying a square pump pulse bias current (see reference 490 in FIG. 1, for example) to the SOA 410, which is synchronized with the round-trip time of the cavity. This constrains the laser 100 to no longer operate with two pulses per round trip, but only one. In this case, there is a secondary coherence peak at 240 mm (2), but not at 120 mm.

Figure 7A:
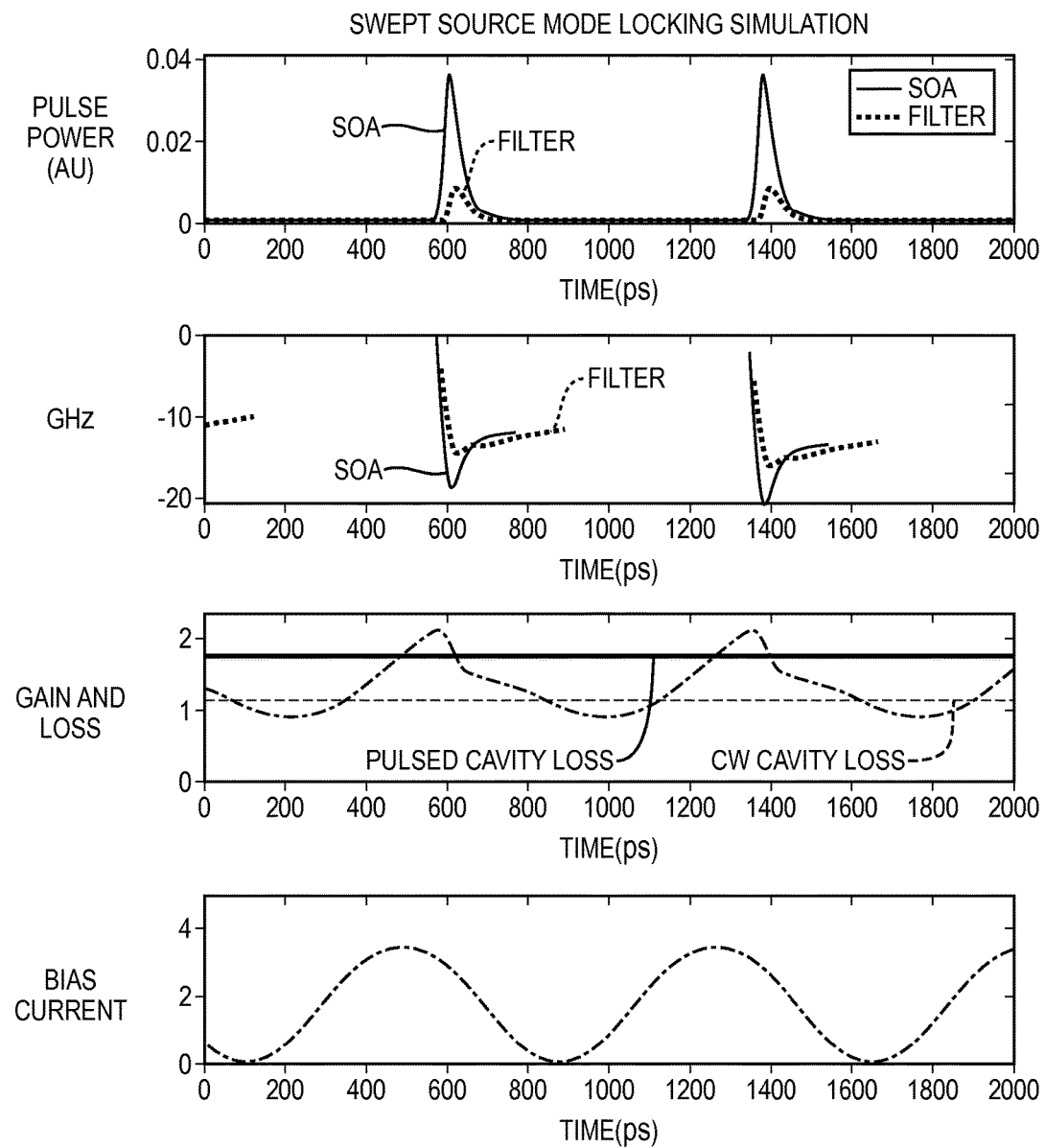
FIG. 7A contains four plots from a computer simulation on a common timescale in picoseconds: optical power for light exiting the SOA 410 and the Fabry-Perot tunable filter 412, the instantaneous optical frequency change in GigaHertz (GHz), the gain from the SOA 410, and the bias current to the SOA 410.
Figure 7B:
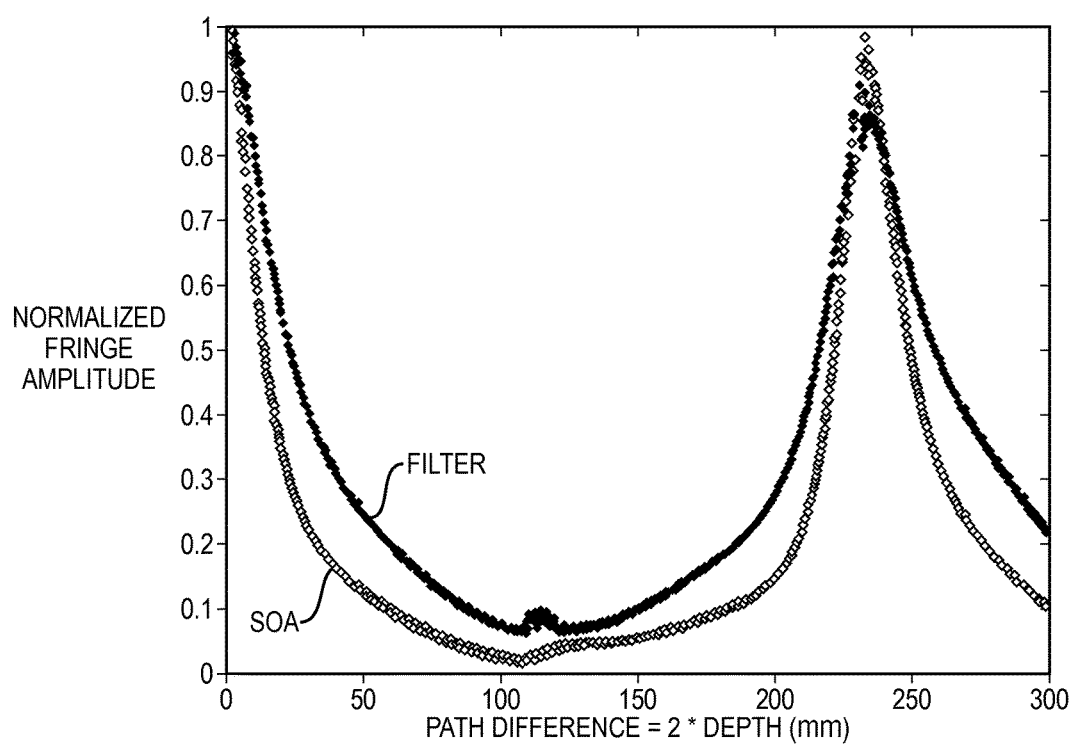
FIG. 7B is a plot of normalized fringe amplitude from a test interferometer as a function of depth in millimeters, illustrating the performance of a tunable with stabilized mode locking during scanning over the tuning band in which only pulse is allowed to circulate within the laser cavity by application of a sinusoidal SOA bias current.

FIGS. 7A and 7B are similar results from another computer simulation. It shows a tunable laser with stabilized swept mode locking. In this case, the laser is again constrained to operate with only 1 pulse per cavity round trip.

The "gated" mode locking is effected by applying a sinusoidal bias current 490 to the SOA 410, which is synchronized with the round-trip time of the cavity to thereby the gain of the laser cavity. This constrains the laser 100 to no longer operate with two pulses per round trip, but only one. In this case, there is a secondary coherence peak only at 240 mm.

Figure 8:
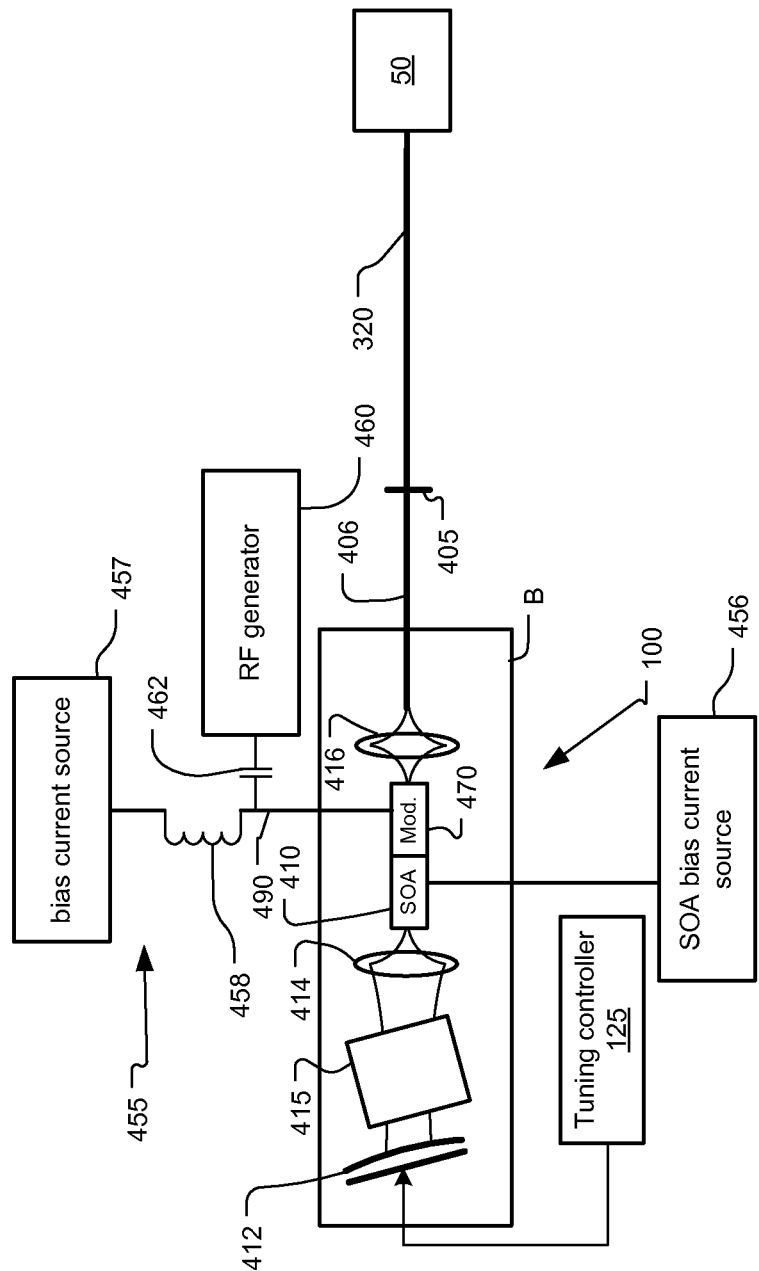
FIG. 8 is a schematic diagram of a linear cavity active mode-locked laser swept source for optical coherence analysis according to a second embodiment the present invention using phase modulation.

FIG. 8 illustrates a second embodiment in which the active mode locking system is implemented as an intra-cavity phase modulator in a linear cavity laser swept source configuration in order to control and stabilize the laser's behavior. Active phase modulation facilitates not only the tuning to lower optical frequencies, but also high speed tuning to higher optical frequencies to thereby enable stable and smooth up and down tuning.

In more detail, a phase modulator 470 is added into the cavity, preferably towards one end of the cavity to control the mode locked operation of the laser. In one embodiment, the phase modulator is installed on the bench B between the SOA 410 and the lens structure 416. In the preferred embodiment, it is a semiconductor chip that is integral with the SOA chip 410 and specifically a phase modulation section to which a separate, modulated bias current or Voltage is supplied to thereby yield a two-section SOA (gain, phase). Integrated phase modulators generally work forward biased through current injection, but reverse biased types also exist.

In other examples, the phase modulator 470 is an external modulator, such as LiNbO$_3$.

SOA gain saturation has a red shifting effect. Gain saturation is not required for an active phase modulated laser embodiment to work.

Preferably, the modulation to the phase modulator 470 is supplied as described previously using a bias current modulation system 455 that includes a radio frequency generator 460 that generates a modulated signal at a harmonic of the cavity round trip frequency. The signal from the RF generator 460 is supplied through a capacitor 462 such that the capacitor 462 in combination with the inductor 458 connected to a bias current source 457 produce a modulated bias current or voltage 490 that is delivered to the phase modulator 470.

Typically in this example, the bias current source 456 for the SOA 410 supplies a DC, unmodulated, signal.

The phase modulator 470 imparts a frequency shift of its own, $(1/2\pi)d\Phi/dt$, as the pulse passes through it. This frequency shift can be positive or negative depending on the pulse's timing. Since the shift can be positive, counteracting the negative frequency shift from gain medium saturation, stable operation can be achieved for positive tuning rates.

The phase modulator 470 is driven at a high harmonic of the round trip time of the long cavity in one example. Complex waveforms and harmonics of the cavity round trip frequency can be also used to drive the phase modulator. In the case of sinusoidal modulation, the modulated phase is $\Phi_{peak} \cos(2\pi f_{mod} t)$. The phase modulator imparts a maximum frequency shift per round trip of $\Phi_{peak} \cdot f_{mod}$. The sign and magnitude of the frequency shift depends on the timing of the pulse with respect to the phase modulation waveform. This provides some tolerance to tuning rate in practical systems.

Figure 9:
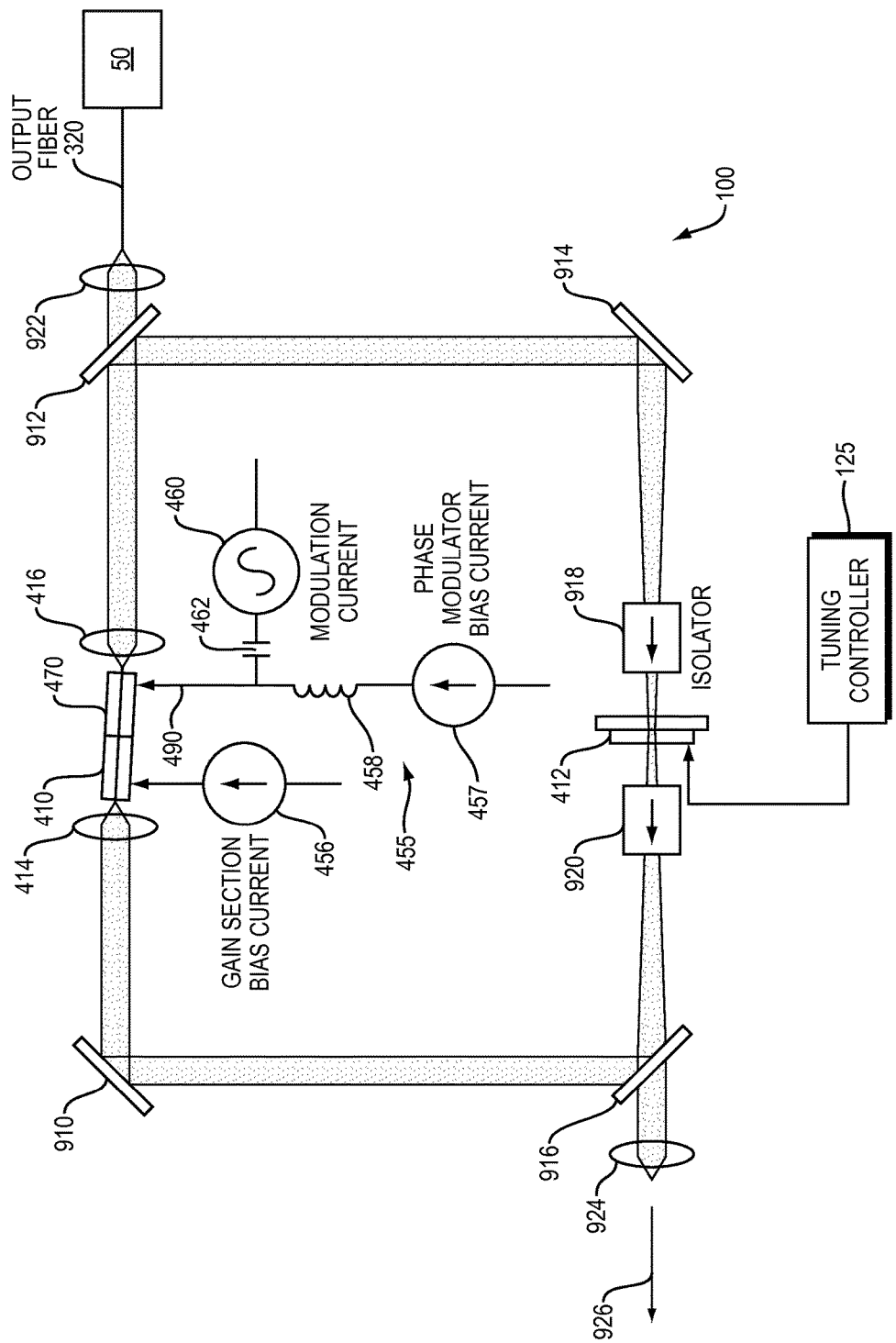
FIG. 9 is a schematic diagram of a phase modulated ring cavity mode-locked laser swept source for optical coherence analysis.

FIG. 9 illustrates another embodiment in which the mode locking system is implemented as an in-cavity phase modulator in a ring cavity, free space laser swept laser configuration.

As before, the phase modulator 470 is shown as located between the SOA 410 and the lens structure 416.

Preferably, the modulation to the phase modulator 470 is supplied as described previously using a radio frequency generator 460 that generates a modulated signal at a harmonic of the cavity round trip frequency to control mode locked operation. The signal from the RF generator 460 is supplied through a capacitor 462 such that the capacitor 462 in combination with the inductor 458 connected to a modulator bias current source 457 produce a modulated bias current or voltage 490 that is delivered to the phase modulator 470.

The phase modulator 470 is an external modulator, such as LiNbO$_3$, in one embodiment, or integrated with the SOA chip 410, in another embodiment. Integrated phase modulators generally work forward biased through current injection, but reverse biased types also exist.

Typically in this example, the bias current source 456 for the SOA 410 supplies a DC, unmodulated, signal.

A series of mirrors 910, 912, 914, and 916 yield a ring cavity configuration. In the illustrated example, the tunable filter 412 is located on an opposite leg of the ring from the SOA 410. In the illustrated example, a first isolator 918 is provided on the upstream side of the tunable filter 412 and a second isolator 920 is provided on the downstream side of the filter 412. These isolators prevent parasitic reflections from the light reflected by the tunable filter 412 and between the isolator 920 and the front facet of the SOA 410. In the illustrated implementation, the optical output is taken from the ring through mirror 912, which is a partially reflecting mirror. An output lens 922 focuses the beam of the swept optical signal on to the entrance facet of the output optical fiber 320 that conveys light to interferometer 50 of the OCT system.

In one implementation, mirror 916 is also partially reflecting. This provides the opportunity to have a second output—or alternate output—swept optical signal 926 that is collimated by lens 924.

In some implementations, the isolators 918 and 920 are not required. Instead, the tunable filter 412 is angled with respect to the optical axis to provide for angle isolation and to spoil any parasitic reflections. In such an embodiment, a Fabry-Perot tunable filter 412 with two flat mirrors is used.

Figure 10:
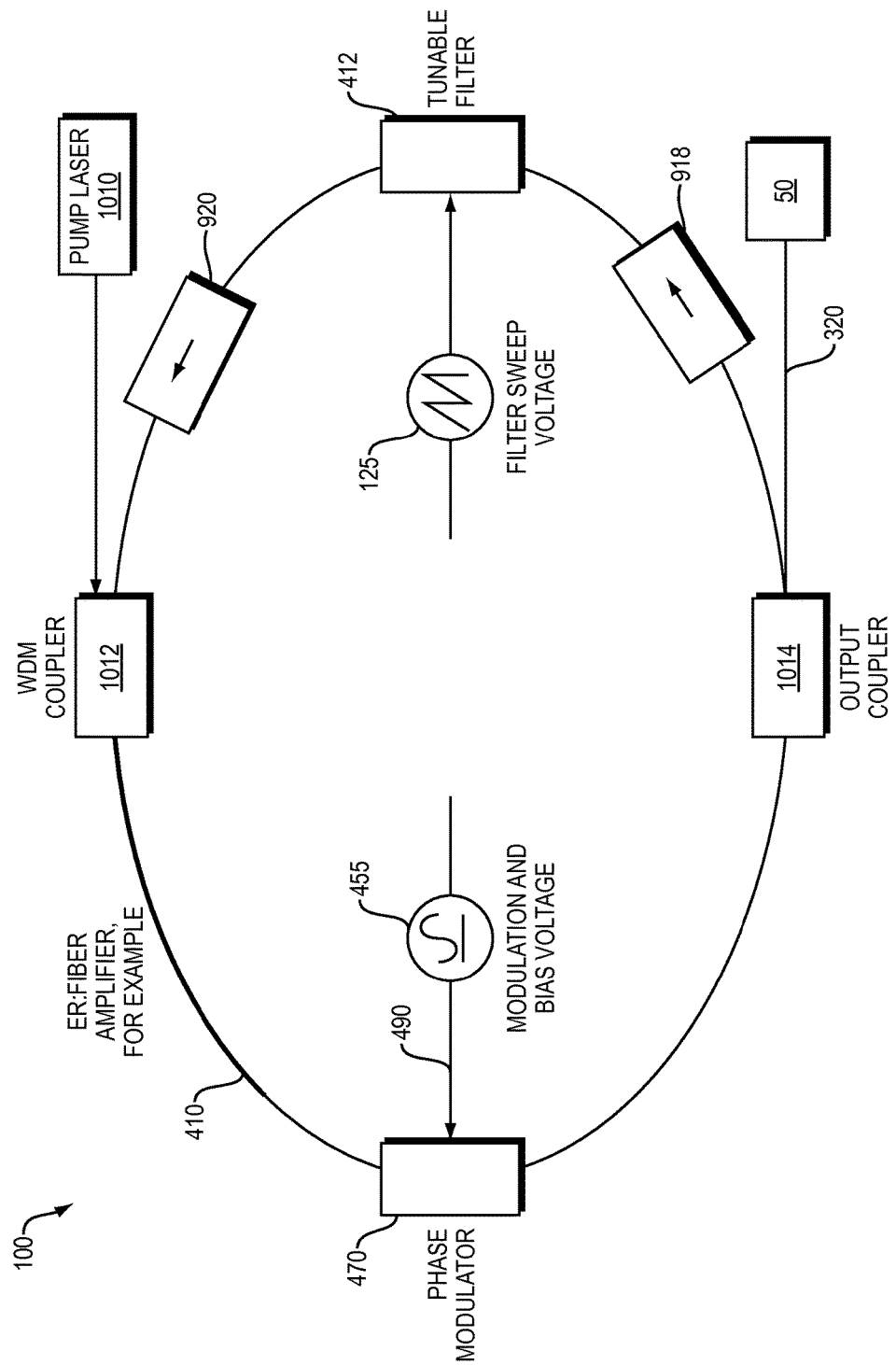
FIG. 10 is a schematic diagram of a phase modulated ring cavity mode-locked fiber laser swept source for optical coherence analysis.

FIG. 10 illustrates another embodiment in which the mode locking system is implemented as an in-cavity phase modulator in a ring cavity fiber laser swept source.

In more detail, the tunable filter 412 is coupled to an upstream fiber isolator 918 and a downstream fiber coupled isolator 920. The downstream isolator 920 is coupled to a wavelength division multiplexing coupler 1012. This WDM coupler 1012 brings in the light from a pump laser 1010. The output of the WDM coupler 1012 is coupled to a fiber amplifier such as an erbium-doped amplifier that functions as the cavity gain element 410. This amplifies light in the fiber ring cavity using the light from the pump laser 1010.

A fiber coupled phase modulator 470 is driven by a modulation and bias voltage 455. The phase modulator 470 is coupled preferably by a fiber to an output coupler 1014 that provides swept optical signal on the output fiber 320 to the interferometer 50 of the OCT system.

A phase modulated laser does not depend on gain saturation for frequency shifting of the pulses. Consequently, gain media 410 with long lifetimes, such as rare-earth doped fiber, is used in this ring laser. This would include Er:fiber and Yb:fiber gain media 410, among others. Although a fiber-based implementation is shown here, versions built using free-space optics could be implemented as well.

Figure 11:
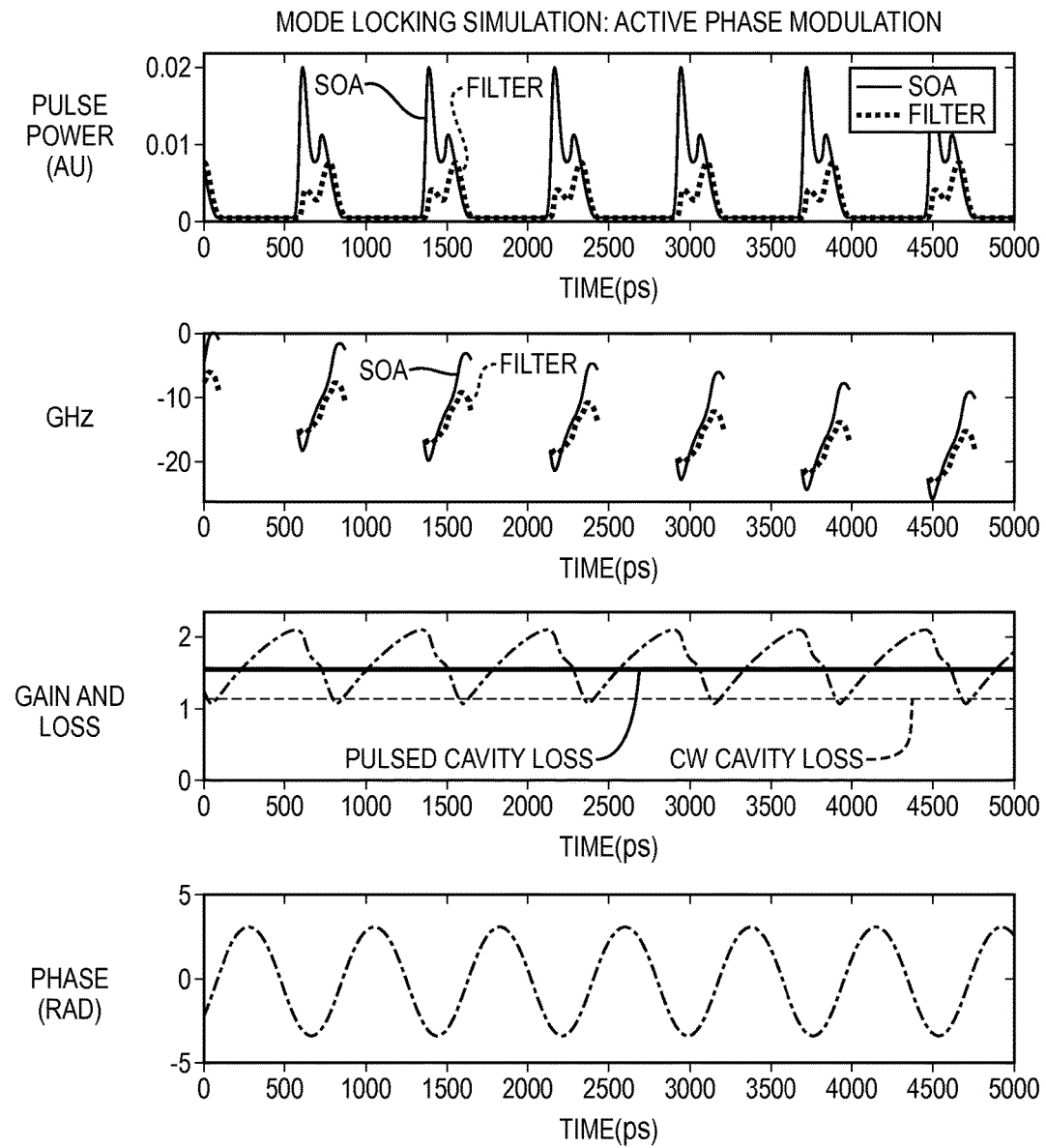
FIG. 11 contains four plots from a computer simulation on a common timescale in picoseconds: optical power for light exiting the SOA/gain element 410 and the Fabry-Perot tunable filter 412, the instantaneous optical frequency change of the pulses in GigaHertz (GHz) at the filter and SOA, the gain from the SOA 410, and the phase shift in radians applied by the phase modulator when tuning at a −2 GHz/ns sweep rate.
Figure 12:
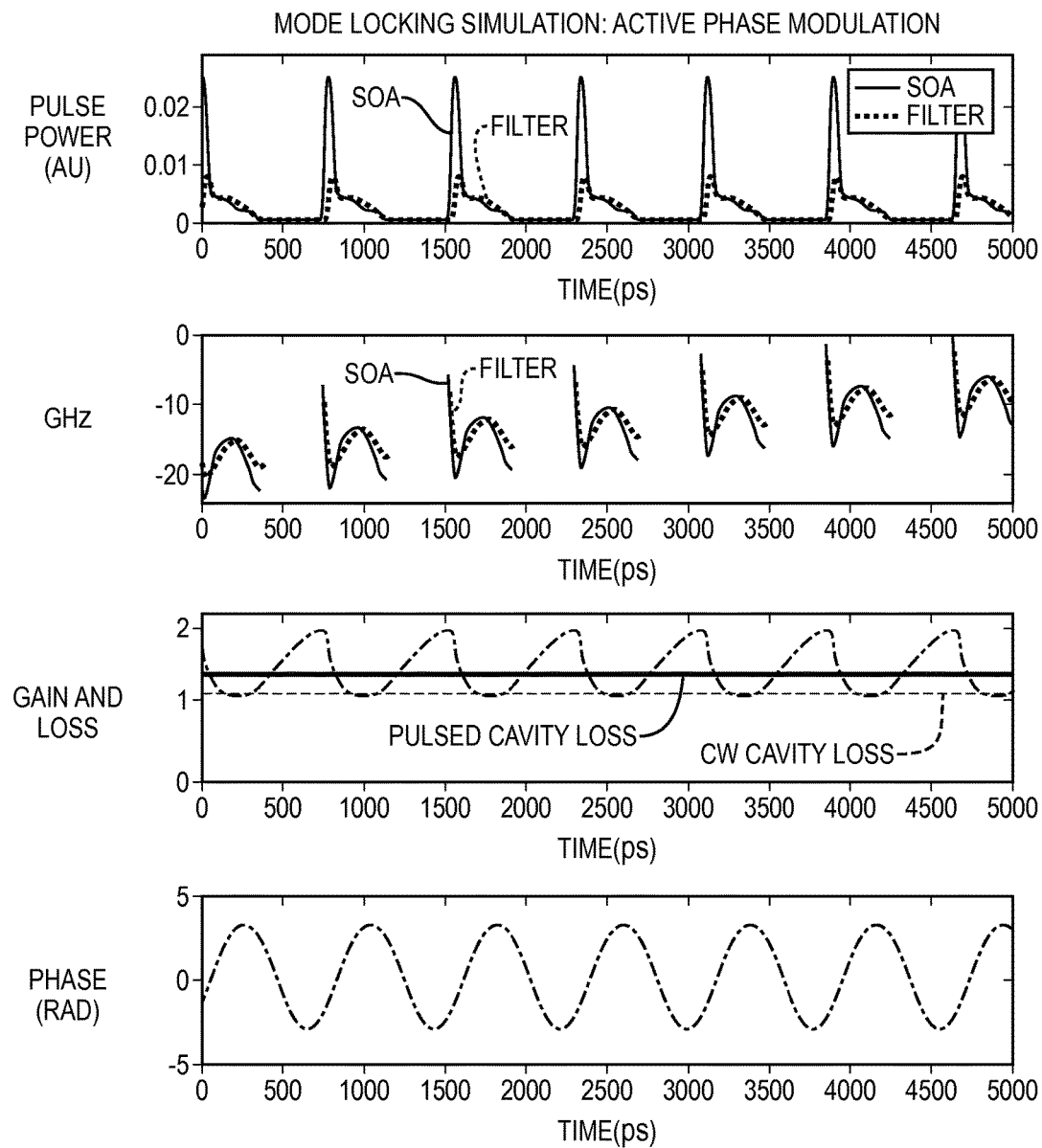
FIG. 12 contains four plots from a computer simulation on a common timescale in picoseconds: optical power for light exiting the SOA/gain element 410 and the Fabry-Perot tunable filter 412, the instantaneous optical frequency change of the pulses in GigaHertz (GHz) at the filter and SOA, the gain from the SOA 410, and the phase shift in radians applied by the phase modulator when tuning at a +2 GHz/ns sweep rate.

FIGS. 11 and 12 are the results of two computer simulations showing the effect of intracavity phase modulation on the performance of the ring lasers. In this case, sinusoidal phase modulation of amplitude it synchronized to the round-trip time of the laser cavity was used as shown by the applied phase shift as a function of time plots.

Modulation of the SOA gain is shown in the "Gain and Loss" plot. The CW cavity loss is shown as a dotted line. The loss for the wavelength swept laser that is pulsed is shown as a solid line.

The laser pulses producing a clean swept optical signal for both positive and negative tuning rates.

At negative tuning rates (FIG. 11), most of the pulse frequency hopping is due to the index modulation resulting from gain saturation of the SOA 412. The pulse passes through the phase modulation near the trough of the sine wave where little additional frequency shift from the phase modulator is imparted.

For positive tuning rates (FIG. 12), the frequency hop from the phase modulator counteracts the hop from the gain saturation. For this to happen, the pulse must pass through the modulator when it has a high positive rate of phase change, dΦ/dt as shown in the phase versus time plot.

Figure 13:
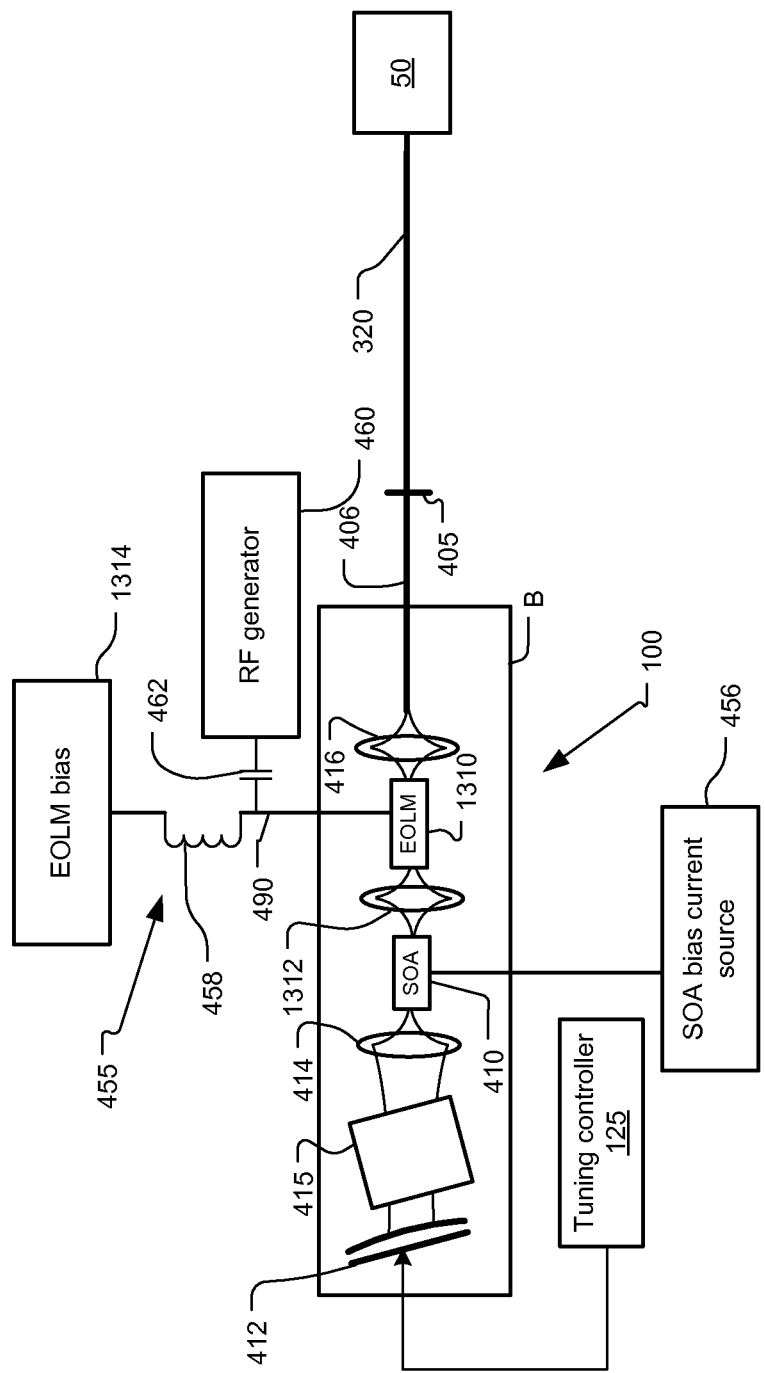
FIG. 13 is a schematic drawing of a loss modulated linear cavity mode-locked laser swept source for optical coherence analysis according to another embodiment the present invention.

FIG. 13 illustrates another embodiment in which the mode locking system is implemented as an in-cavity electro-optic loss modulator 1310 in a linear cavity laser swept source configuration.

In more detail, an electro-optic loss modulator 1310 is added into the cavity, preferably towards one end of the cavity, to control the mode locked operation. It is used to modulate the gain of the laser cavity. In one embodiment, the electro-optic loss modulator (EOLM) 1310 is installed on the bench B between the SOA 410 and the lens structure 416. An intervening lens 1312 couples light between the SOA 410 and the EOLM 1300.

Preferably, the modulation to the electro-optic loss modulator 1310 is supplied as described previously using a bias current modulation system 455 including a radio frequency generator 460 that generates a modulated signal at a harmonic of the cavity round trip frequency. The signal from the RF generator 460 is supplied through a capacitor 462 such that the capacitor 462 in combination with the inductor 458 connected to an EOLM bias voltage or current 1314 produce a modulated bias current or voltage 490 that is delivered to the electro-optic loss modulator 1310.

Typically in this example, the bias current source 456 for the SOA 410 supplies a DC, unmodulated, signal.

Figure 14:
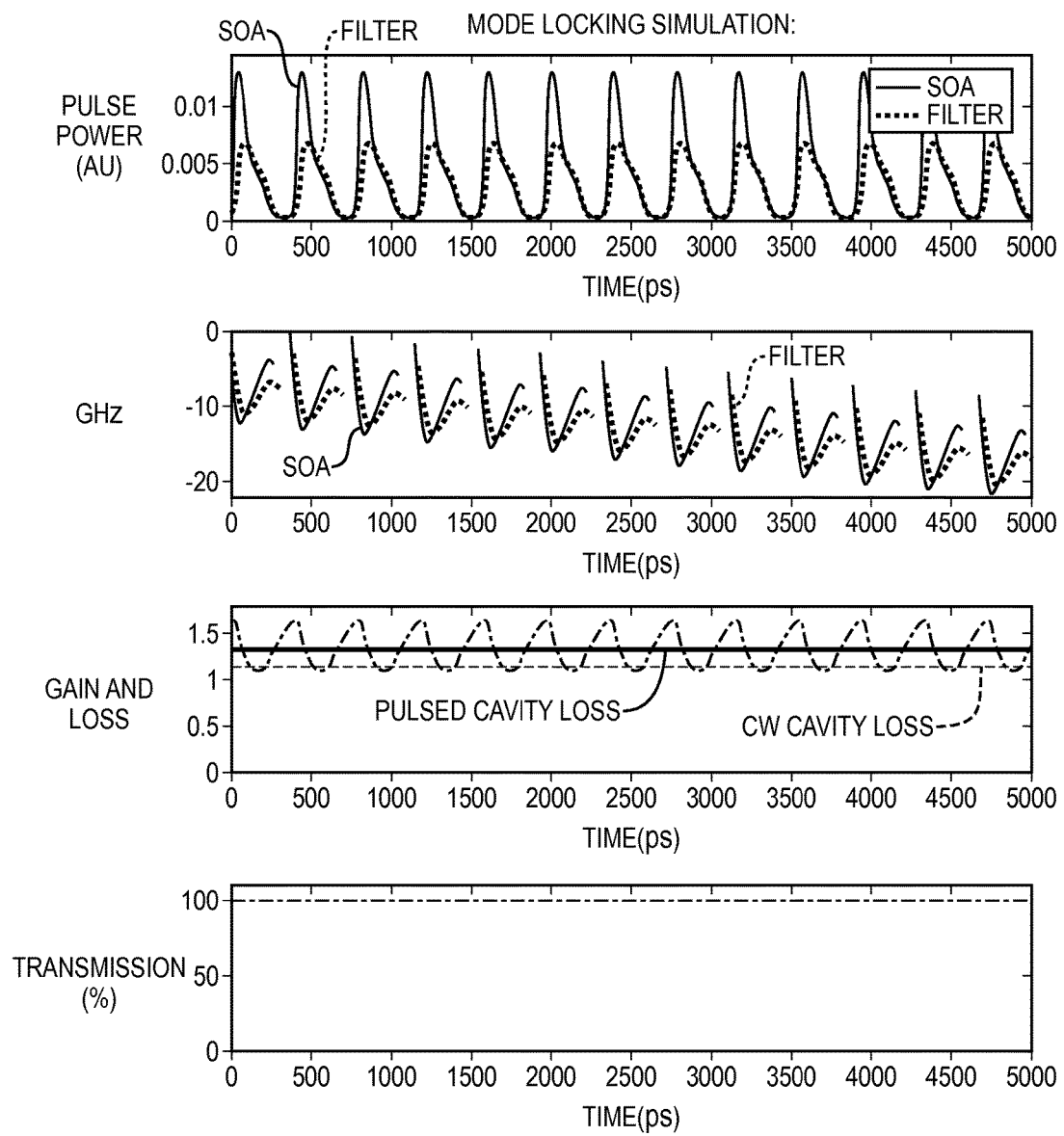
FIG. 14 contains four plots from a computer simulation on a common timescale in picoseconds: optical power for light exiting the SOA/gain element 410 and the Fabry-Perot tunable filter 412, the instantaneous optical frequency change of the pulses in GigaHertz (GHz) at the filter and SOA, the gain from the SOA 410, and the loss applied by the loss modulator 1310 (unmodulated in this case)

FIG. 14 shows the results of a computer simulation for normal swept mode locking without loss modulation—the EOLM transmission is 100%. In this case, the laser operates with 2 pulses per cavity round trip.

Figure 15:
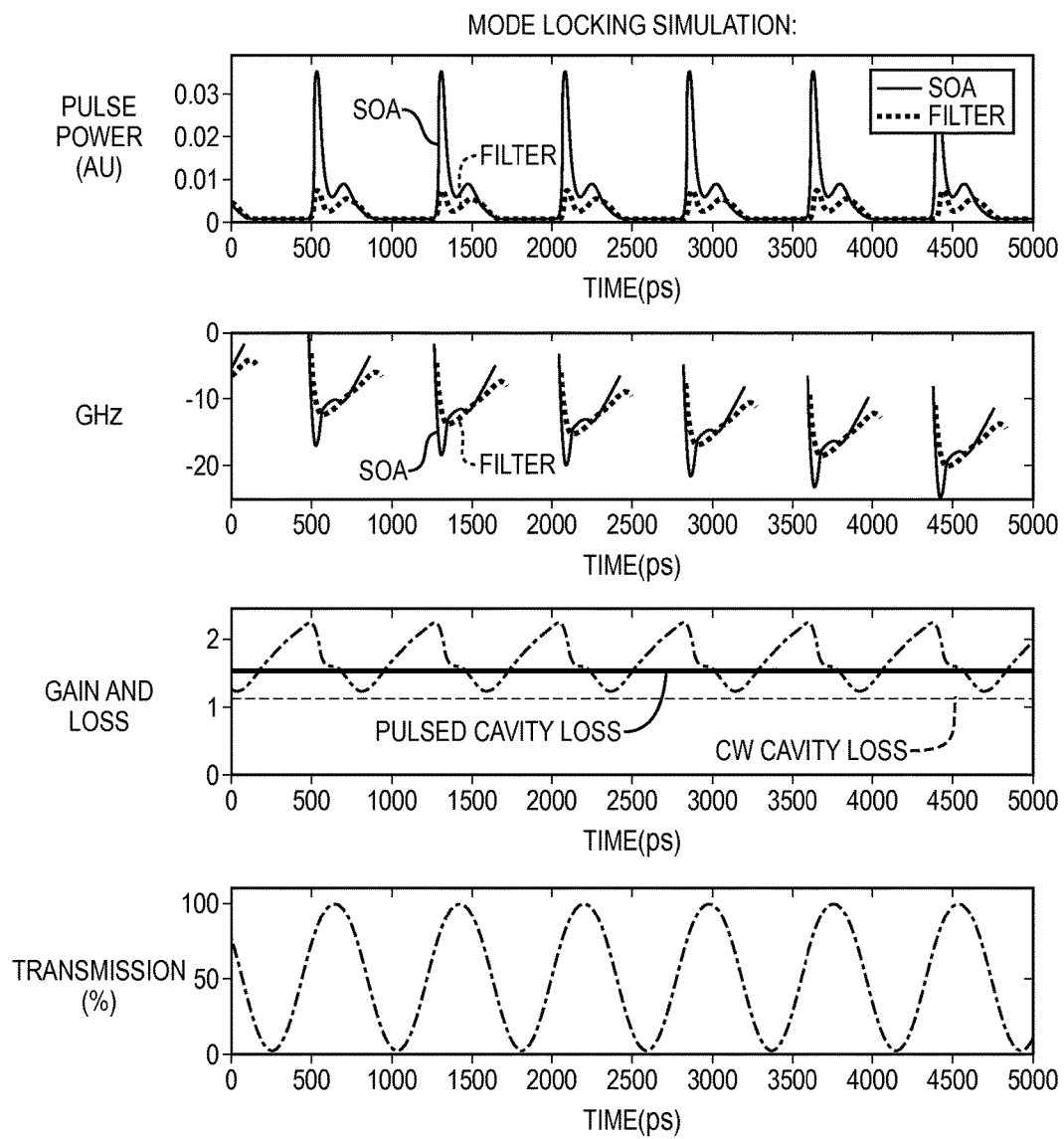
FIG. 15 contains four plots from a computer simulation on a common timescale in picoseconds: optical power for light exiting the SOA/gain element 410 and the Fabry-Perot tunable filter 412, the instantaneous optical frequency change of the pulses in GigaHertz (GHz) at the filter and SOA, the gain from the SOA 410, and the modulated loss applied by the loss modulator 1310.

FIG. 15 shows the results of a computer simulation for swept mode locking with loss modulation. In the illustrated example, the laser operates in a gated mode locked condition. The loss modulation is illustrated in the bottom plot which shows the EOLM transmission as a function of time. The laser changes operation from 2 to 1 pulses per round trip at the same negative tuning rate (GHz/ns).

In the example, this is a type of active "gated" mode locking, but the modulation could be synchronized with any harmonic of the round trip time, and would not have to be a sinusoidal waveform either.

In the illustrated embodiment, the loss modulation is performed by a high-speed EOLM modulator 1310. In other embodiments, waveguide Mach-Zehnder loss modulators, standing wave acousto-optic "mode-lockers", electro-absorption modulators, in either linear or ring configurations are implemented. Most technologies mandate that the modulation be separate from the SOA 410, although some technologies allow integration with the SOA chip.

Figure 16:
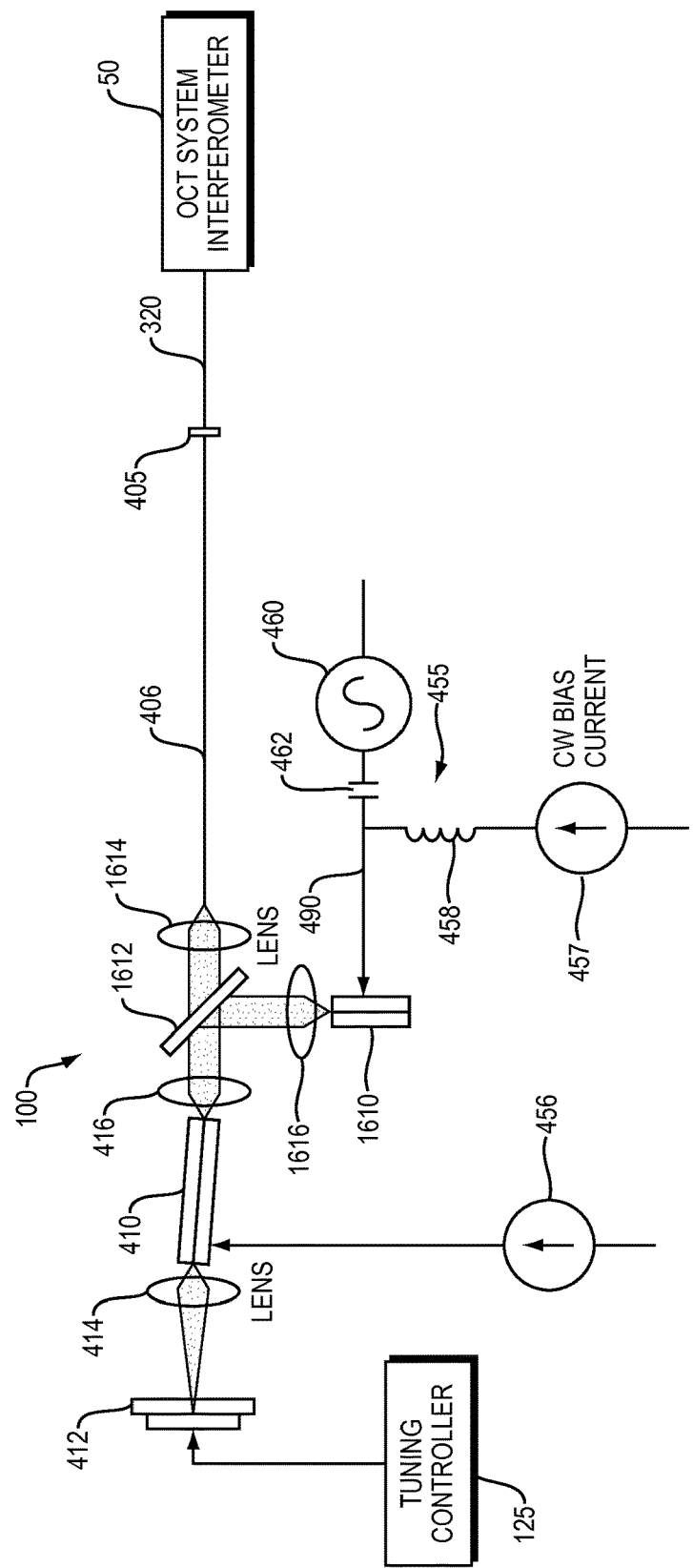
FIG. 16 is a schematic diagram showing a linear cavity mode-locked laser swept source for optical coherence analysis that utilizes synchronous pumping to control the mode-locked operation.

FIG. 16 shows a mode-locked laser swept source 100 for optical coherence analysis that utilizes synchronous pumping to control and stabilize the mode-locked operation by modulating the gain of the laser cavity.

A linear cavity configuration is shown with the frequency tuning Fabry-Perot filter 412 defining one end of the cavity, in the illustrated implementation.

The cavity extends to a second output reflector 405 that is located at the end of a fiber pigtail 406 that also forms part of the cavity.

Light passing through the output reflector 405 is transmitted on optical fiber 320 or via free space to an interferometer 50 of the OCT system.

The semiconductor optical amplifier (SOA) chip gain element 410 is located within the laser cavity. In the current embodiment, input and output facets of the SOA chip 410 are angled and anti-reflection (AR) coated, providing parallel beams from the two facets.

Each facet of the SOA 410 has an associated lens structure 414, 416 that is used to couple the light exiting from either facet of the SOA 410. The first lens structure 414 couples the light between the back facet of the SOA 410 and the reflective Fabry-Perot tunable filter 412. Light exiting out the output or front facet of the SOA 410 is coupled by the second lens structure 416 to a fiber end facet of the pigtail 406.

The tuning controller 125 provides a tuning voltage function to the Fabry-Perot filter 412 that sweeps the passband optical frequency across the tuning band, preferably with optical frequency varying linearly with time.

The mode locking system of the illustrated embodiment includes a bias current modulation system 455 that modulates bias applied to a pump laser 1610.

In the illustrated example, the light from pump laser 1610 is coupled to the laser cavity using a WDM mirror 1612 and two additional lenses 1614, 1616.

In more detail, light exiting from pump laser 1610 is collimated by pump lens 1616. It is directed to the WDM mirror 1612 that is configured to reflect light at the pump wavelength but transmit the light exiting from the laser cavity, i.e., within the laser's tuning band. Thus laser light is collimated by output lens 1614 and coupled to the fiber pigtail 406, whereas pump light is coupled in to the cavity.

The SOA laser bias current source 456 supplies a direct current for the bias current supplied to the SOA 410.

In contrast, the pump laser bias current source 455 generates a modulated bias current 490 using a radio frequency generator 460 that generates an electronic signal having a frequency of a harmonic of the cavity round trip frequency. This frequency corresponds to the time required for light to make a round trip in the cavity of the laser 100.

In the illustrated laser, this corresponds to twice the time required for light to propagate from the tunable filter 412 at one end of the cavity to the output reflector 405, which is at the end of the pigtail 406, in one implementation.

The signal from the RF generator is supplied through a capacitor 462 such that the capacitor 462 in combination with the inductor 458 yield a modulated bias current 490 that is delivered to the pump laser 1610.

In this synchronous pumping embodiment, the light from the pump laser 1610, e.g. 980 nm semiconductor laser chip, is absorbed by the longer wavelength SOA gain medium 410. The SOA 410 is "pumped" by the pump laser 1610, possibly in addition to direct electrical pumping from a CW current source 456.

The advantage of this configuration is that the pump laser pulses, through a gain switching mechanism have the capacity to be much shorter that the electrical modulation pulse or sinusoidal drive period. This means that the SOA gain can be pumped up in a shorter time period than it could be by direct electronic modulation as illustrated with respect to the embodiment of FIG. 1, for example.

In addition, the pump 1610 is a mode locked laser, in one embodiment. In this way, the natural pulsed behavior of the mode locked laser synchronously pumps laser cavity without the need for complex high-frequency electronic drive current sources.

This approach is applied using a ring cavity configuration, in other embodiments.

Figure 17:
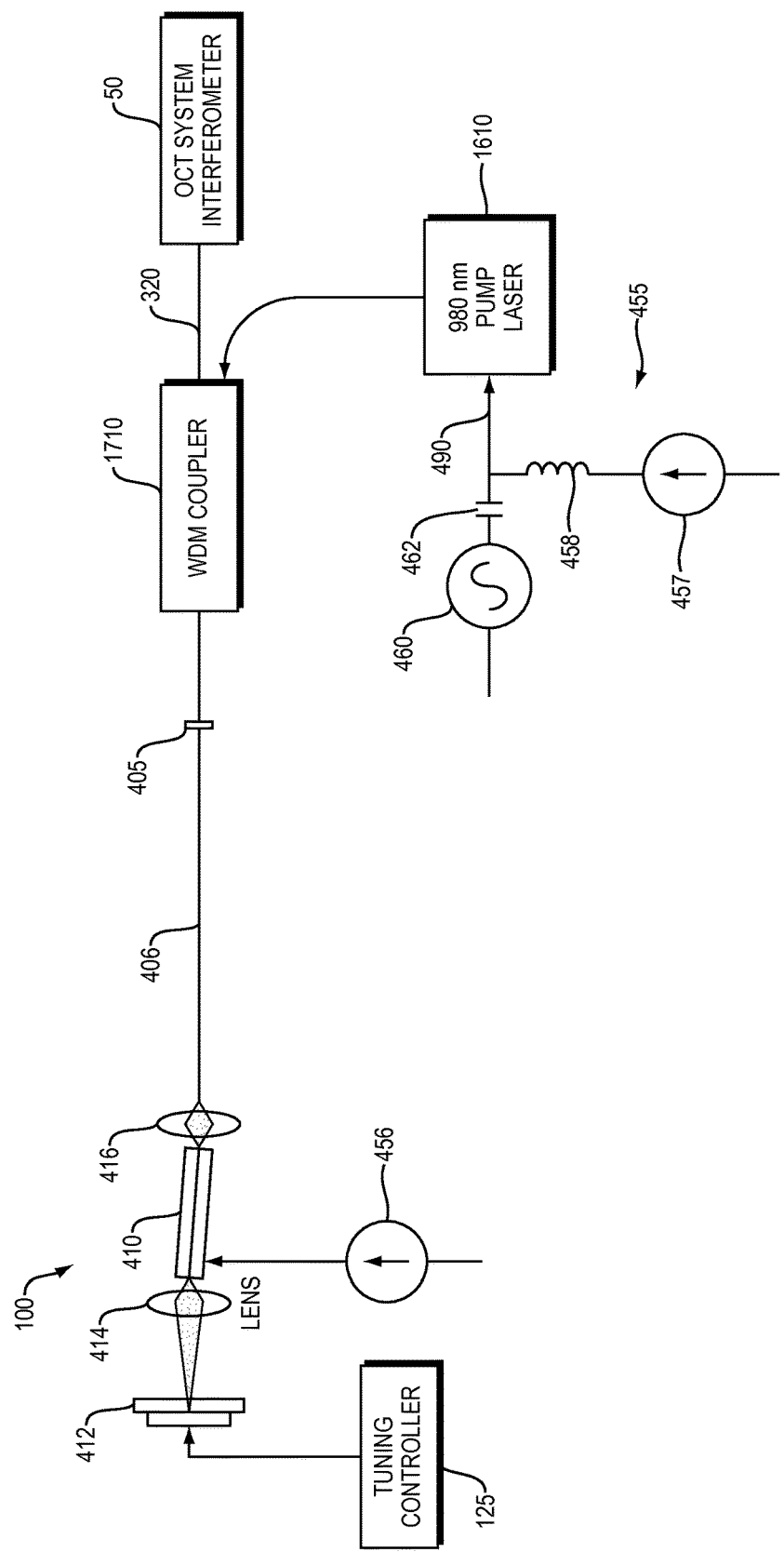
FIG. 17 is a schematic diagram showing a related embodiment that uses a hybrid, free space laser cavity utilizing synchronous pumping to control the mode-locked operation.

FIG. 17 shows a related embodiment using a hybrid, free space approach. In this example, the light from the pump laser 1610 is coupled into the laser cavity via the WDM fiber coupler 1710.

Figure 18:
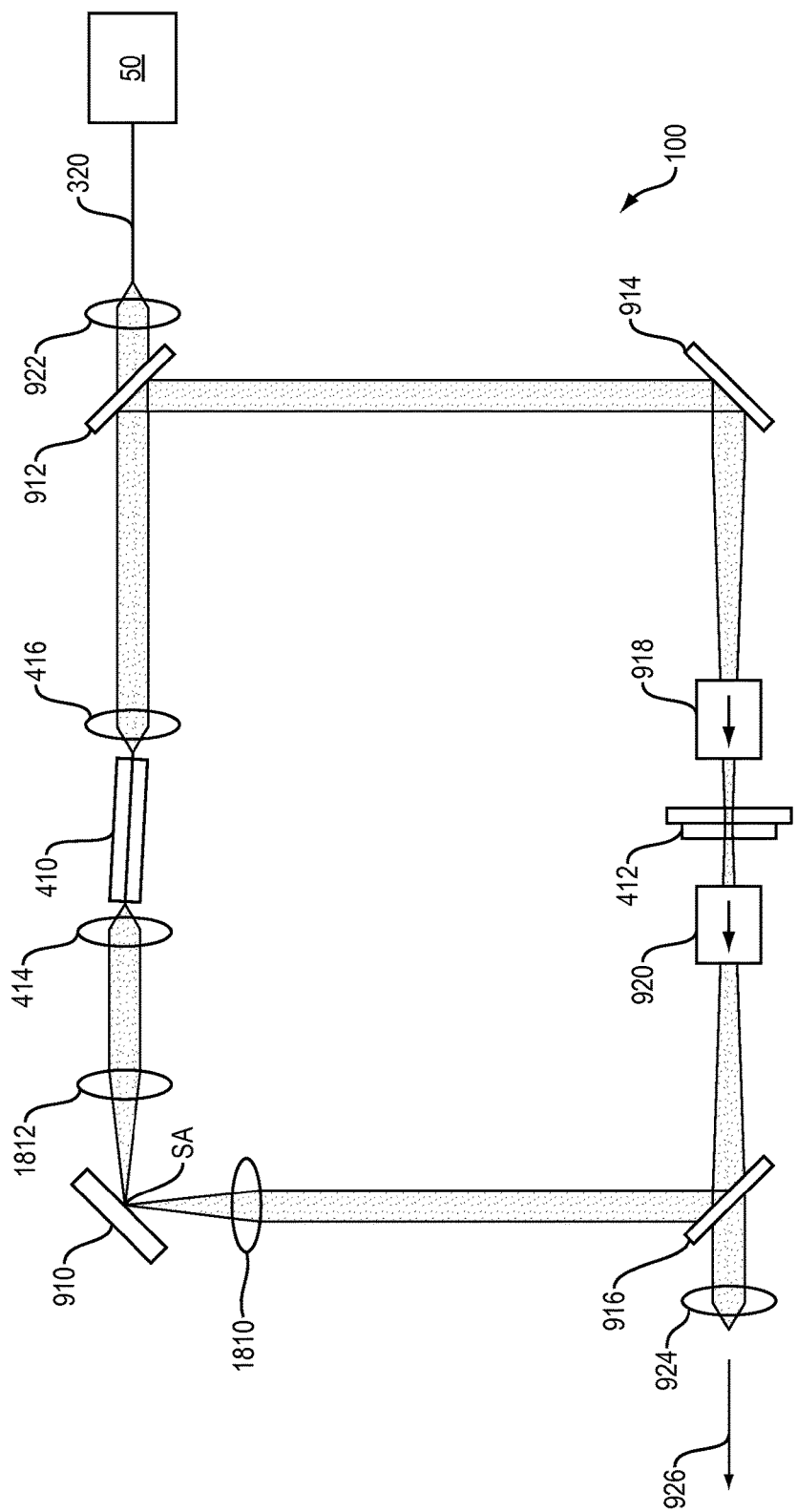
FIG. 18 is a schematic diagram showing a ring cavity mode-locked laser swept source for optical coherence analysis using a saturable absorber mirror to control the mode-locked operation.

FIG. 18 illustrates another embodiment in which the mode locking control system is implemented using a saturable absorber in a ring cavity laser swept source 100 in order to modulate the gain of the laser cavity and thereby control the mode locked operation.

A series of mirrors 910, 912, 914, and 916 yield a ring cavity configuration. In the illustrated example, the tunable filter 412 is located on an opposite leg of the ring from the SOA 410. In the illustrated example, a first isolator 918 is provided on the upstream side of the tunable filter 412 and a second isolator 920 is provided on the downstream side of the filter 412. These isolators prevent parasitic reflections from the light reflected by the tunable filter 412 and between the isolator 920 and the front facet of the SOA 410.

In the illustrated implementation, the swept optical signal is taken from the ring through mirror 912, which is a partially reflecting mirror. An output lens 922 focuses the beam of the swept optical signal on to the entrance facet of the output optical fiber 320 that conveys light to interferometer 50 of the OCT system.

In one implementation, mirror 916 is also partially reflecting. This provides the opportunity to have a second output signal 926 that is collimated by lens 924.

This embodiment implements a form of passive mode locking to help stabilize swept operation into regular pulsation. This is accomplished by adding a saturable absorber SA 910 to the laser cavity. In the ring configuration, this is most easily done by placing the saturable absorber SA in contact with one of the mirrors, such as mirror 910.

Semiconductor saturable absorber mirrors (SESAM) and carbon nanotubes (see F. Wang et al., "Wideband-tuneable, Nanotube Mode-locked, Fibre Laser," Nature Nanotechnology, VOL 3, DECEMBER 2008, pp. 738-742) are two examples of suitable materials. Two additional lenses 1810 and 1812 are preferably added to the ring cavity to couple light in and out of the saturable absorber mirror SA 910. The lenses 1810 and 1812 function to reduce the beam waist so that the absorber SA 910 saturates more easily than the gain medium, a condition for passive mode locking See Herman A. Haus, "Mode-Locking of Lasers," IEEE JOURNAL ON SELECTED TOPICS IN QUANTUM ELECTRONICS, VOL. 6, NO. 6, NOVEMBER/DECEMBER 2000, pp. 1173-1185.

FIGS. 19 and 20 illustrate further embodiments in which the mode locking control system is implemented using a saturable absorber in linear cavities of the laser swept source 100 in order to modulate the gain of the laser cavity.

In FIG. 19, the laser cavity extends between the tunable filter 412 through lenses 414, 416, SOA 410 to a saturable absorber mirror SESAM. In order to get low saturation power, another lens 1910 is added to focus the beam onto the saturable absorber mirror SESAM.

In this embodiment, the output is taken through the tunable filter 412. In more detail, light transmitted to the tunable filter is focused by lens 1912 on to the output optical fiber 320 that conveys the swept optical signal to the OCT system interferometer 50.

FIG. 20 shows a similar configuration. However this embodiment utilizes a transmissive saturable absorber 1914. In more detail, lens 1910 focuses the cavity beam so that a focal point is within the saturable absorber 1914. A second lens 1916 on the other side of the saturable absorber 1914 recollimates the beam, which is reflected from mirror 1918 that defines the end of the laser cavity.

This configuration will promote operation with 3 pulses in the cavity when the saturable absorber 1914 is located at one third of a cavity from an end mirror, such as mirror 1918. Adjacent pulses will collide in the saturable absorber 1914, helping each other to saturate the absorption.

Figure 21:
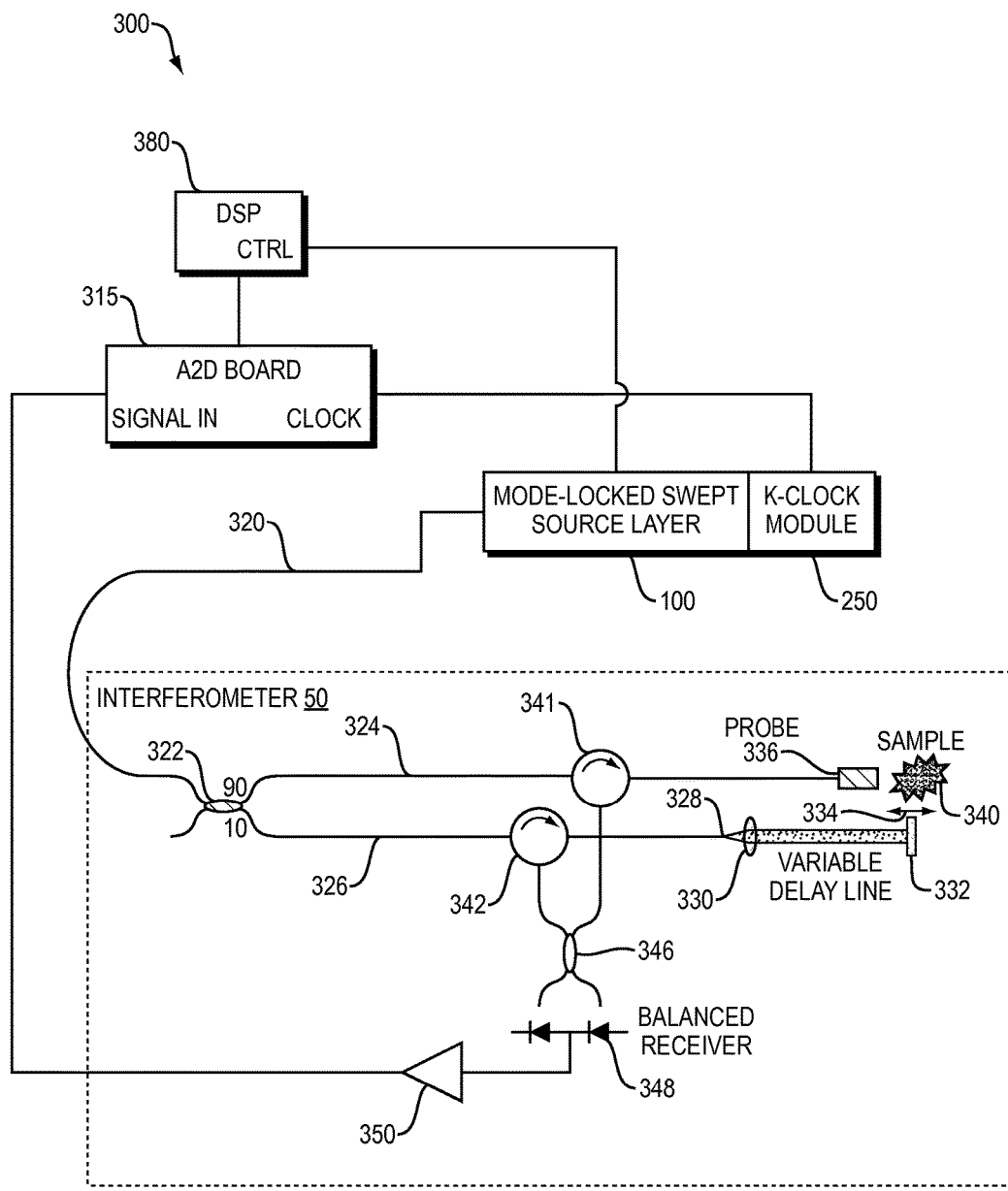
FIG. 21 is a schematic view of an OCT system incorporating the mode-locked laser swept source according to an embodiment of the invention.

FIG. 21 shows an optical coherence analysis system 300 using the mode locked laser source 100, which has been constructed according to the principles of the present invention.

The tunable laser swept source 100 with stabilized mode locked operation generates the tunable or swept optical signal on optical fiber 320 that is transmitted to interferometer 50. The swept optical signal scans over a scanband with a narrowband emission.

Preferably, a k-clock module 250 is used to generate a clocking signal at equally spaced optical frequency increments as the optical signal is tuned or swept over the scan or tuningband.

In the current embodiment, a Mach-Zehnder-type interferometer 50 is used to analyze the optical signals from the sample 340. The tunable signal from the swept laser source 100 is transmitted on fiber 320 to a 90/10 optical coupler 322. The combined tunable signal is divided by the coupler 322 between a reference arm 326 and a sample arm 324 of the system.

The optical fiber of the reference arm 326 terminates at the fiber endface 328. The light exiting from the reference arm fiber endface 328 is collimated by a lens 330 and then reflected by a mirror 332 to return back, in some exemplary implementations.

The external mirror 332 has an adjustable fiber to mirror distance (see arrow 334), in one example. This distance determines the depth range being imaged, i.e. the position in the sample 340 of the zero path length difference between the reference arm 326 and the sample arm 324. The distance is adjusted for different sampling probes and/or imaged samples. Light returning from the reference mirror 332 is returned to a reference arm circulator 342 and directed to a 50/50 fiber coupler 346.

The fiber on the sample arm 324 terminates at the sample arm probe 336. The exiting swept optical signal is focused by the probe 336 onto the sample 340. Light returning from the sample 340 is returned to a sample arm circulator 341 and directed to the 50/50 fiber coupler 346. The reference arm signal and the sample arm signal are combined in the fiber coupler 346 to generate an interference signal. The interference signal is detected by a balanced receiver, comprising two detectors 348, at each of the outputs of the fiber coupler 346. The electronic interference signal from the balanced receiver 348 is amplified by amplifier 350.

An analog to digital converter system 315 is used to sample the interference signal output from the amplifier 350. Frequency clock and sweep trigger signals derived from the k-clock module 250 of the mode-locked swept source 100 are used by the analog to digital converter system 315 to synchronize system data acquisition with the frequency tuning of the swept source system 100.

Once a complete data set has been collected from the sample 340 by spatially raster scanning the focused probe beam point over the sample, in a Cartesian geometry, x-y, fashion or a cylindrical geometry theta-z fashion, and the spectral response at each one of these points is generated from the frequency tuning of the mode-locked swept source 100, the digital signal processor 380 performs a Fourier transform on the data in order to reconstruct the image and perform a 2D or 3D tomographic reconstruction of the sample 340. This information generated by the digital signal processor 380 can then be displayed on a video monitor.

In one application, the probe is inserted into blood vessels and used to scan the inner wall of arteries and veins. In other examples, other analysis modalities are included in the probe such as intravascular ultrasound (IVUS), forward looking IVUS (FLIVUS), high-intensity focused ultrasound (HIFU), pressure sensing wires and image guided therapeutic devices.

While this invention has been particularly shown and described with references to preferred embodiments thereof, it will be understood by those skilled in the art that various changes in form and details may be made therein without departing from the scope of the invention encompassed by the appended claims. For example, although the invention has been described in connection with an OCT or spectroscopic analysis only, the invention could also be applied along with IVUS, FLIVUS, HIFU, pressure sensing wires and image guided therapeutic devices.

What is claimed is:

1. An optical coherence imaging method, comprising:
providing a laser swept source having a laser cavity that is less than a meter long and defined between a Fabry-Perot tunable filter and an output coupler at one end of a fiber;
controlling a swept mode-locked operation of the laser swept source by actively modulating cavity gain by applying a bias current to a gain element in the laser cavity, synchronized with a round trip time of the laser cavity to produce one laser pulse per round trip, and generating a swept optical signal by tuning the Fabry-Perot tunable filter with a tunable filter sweep rate that is several orders of magnitude smaller than a laser cavity round trip rate and the tunable filter sweep rate is greater than 20 kHz, and the laser cavity round trip rate is greater than 1 GHz;
transmitting the swept optical signal to an interferometer having a reference arm and a sample arm, in which a sample is located;
combining the swept optical signal returning from the sample arm and the reference arm to generate an interference signal;
detecting the interference signal; and
generating image information of the sample from the detected interference signal.

2. A method as claimed in claim 1, wherein the laser swept source further comprises an intracavity phase modulator configured to be driven at a rate related to the round trip time of the laser cavity.

3. The method as claimed in claim 1, wherein the bias current has one of: a square or a sinusoidal waveform.

4. An optical coherence imaging method, comprising:
providing a laser swept source having a laser cavity that is less than a meter long and defined between a Fabry-Perot tunable filter and an output coupler at one end of a fiber, the laser swept source further comprising a semiconductor optical amplifier (SOA) chip having a gain section, and an intracavity phase modulator configured to be driven at a rate related to the round trip time of the laser cavity, wherein the phase modulator is integral with the SOA chip and configured to be driven at a harmonic of the round trip frequency of the laser cavity by a bias source different from a bias source for the gain section;
controlling a swept mode-locked operation of the laser swept source by actively modulating cavity gain by applying a bias current to the gain section synchronized with a round trip time of the laser cavity to produce one laser pulse per round trip, and generating a swept optical signal;
transmitting the swept optical signal to an interferometer having a reference arm and a sample arm, in which a sample is located;
combining the swept optical signal returning from the sample arm and the reference arm to generate an interference signal;
detecting the interference signal; and
generating image information of the sample from the detected interference signal.

* * * * *